US012735482B2

(12) United States Patent
Zhang et al.

(10) Patent No.: US 12,735,482 B2
(45) **Date of Patent: *Sep. 15, 2026**

(54) HUMANIZED CD19 ANTIBODY AND USE THEREOF

(71) Applicant: GRACELL BIOSCIENCE (SHANGHAI) CO., LTD., Shanghai (CN)

(72) Inventors: Hua Zhang, Shanghai (CN); Lianjun Shen, Shanghai (CN); Huan Shi, Shanghai (CN); Wei Cao, Shanghai (CN); Wenjie Yin, Shanghai (CN)

(73) Assignee: GRACELL BIOSCIENCE (SHANGHAI) CO., LTD., Shanghai (CN)

( * ) Notice: Subject to any disclaimer, the term of this patent is extended or adjusted under 35 U.S.C. 154(b) by 791 days.

This patent is subject to a terminal disclaimer.

(21) Appl. No.: 17/923,295

(22) PCT Filed: May 6, 2021

(86) PCT No.: PCT/CN2021/091956

§ 371 (c)(1),
(2) Date: Nov. 4, 2022

(87) PCT Pub. No.: WO2021/223720

PCT Pub. Date: Nov. 11, 2021

(65) Prior Publication Data

US 2023/0235052 A1 Jul. 27, 2023

(30) Foreign Application Priority Data

May 6, 2020 (CN) ........................ 202010374769.5

(51) Int. Cl.

| | |
|---|---|
| ***C07K 16/28*** | (2006.01) |
| ***A61K 39/00*** | (2006.01) |
| ***A61K 40/11*** | (2025.01) |
| ***A61K 40/31*** | (2025.01) |
| ***A61K 40/42*** | (2025.01) |
| ***A61P 35/00*** | (2006.01) |
| ***A61P 35/02*** | (2006.01) |
| ***C07K 14/705*** | (2006.01) |
| ***C07K 14/725*** | (2006.01) |
| ***C07K 19/00*** | (2006.01) |
| ***C12N 5/10*** | (2006.01) |
| ***C12N 15/62*** | (2006.01) |

(52) U.S. Cl.

CPC .......... *C07K 16/2803* (2013.01); *A61K 40/11* (2025.01); *A61K 40/31* (2025.01); *A61K 40/4211* (2025.01); *A61K 40/4215* (2025.01); *A61P 35/00* (2018.01); *C07K 14/7051* (2013.01); *C07K 16/2878* (2013.01); *A61K 2039/505* (2013.01); *A61K 2039/5156* (2013.01); *A61K 2239/13* (2023.05); *A61K 2239/21* (2023.05); *A61K 2239/22* (2023.05); *A61K 2239/28* (2023.05); *A61K 2239/29* (2023.05); *A61K 2239/48* (2023.05); *C07K 2317/24* (2013.01); *C07K 2317/31* (2013.01); *C07K 2317/622* (2013.01); *C07K 2317/73* (2013.01); *C07K 2317/76* (2013.01); *C07K 2317/92* (2013.01); *C07K 2319/02* (2013.01); *C07K 2319/03* (2013.01); *C07K 2319/33* (2013.01)

(58) Field of Classification Search

CPC ............ C07K 16/2803; C07K 16/7051; C07K 16/2878; A61K 40/4215

See application file for complete search history.

(56) References Cited

U.S. PATENT DOCUMENTS

| | | | | |
|---|---|---|---|---|
| 4,816,397 | A | 3/1989 | Boss et al. | |
| 4,816,567 | A | 3/1989 | Cabilly et al. | |
| 5,350,674 | A | 9/1994 | Boenisch et al. | |
| 5,585,089 | A | 12/1996 | Queen et al. | |
| 5,585,362 | A | 12/1996 | Wilson et al. | |
| 6,326,193 | B1 | 12/2001 | Liu et al. | |
| 10,493,139 | B2 * | 12/2019 | Wu | C07K 16/2803 |
| 11,840,575 | B2 * | 12/2023 | Zhang | A61K 40/11 |

FOREIGN PATENT DOCUMENTS

| | | | |
|---|---|---|---|
| CN | 104583230 | A | 4/2015 |
| CN | 107383196 | A | 11/2017 |
| CN | 109021114 | A | 12/2018 |

(Continued)

OTHER PUBLICATIONS

"CRISPR-Cas9 genome editing for cancer immunotherapy: opportunities and challenges," Cheng et al, Briefings in Functional Genomics, 19(3), 2020, 183-190 (Year: 2019).*

(Continued)

*Primary Examiner* — Juliet C Switzer

*Assistant Examiner* — Katherine Ann Holtzman

(74) *Attorney, Agent, or Firm* — NKL Law; Allen Xue

(57) ABSTRACT

A humanized CD 19 antibody, and a chimeric antigen receptor thereof, an immune cell thereof and the use thereof are provided. The humanized CD19 antibody is based on a FMC63 chimeric antibody, which is subjected to humanization modification. A CAR-T and a dual CAR-T cell constructed based on the humanized antibody and the related use thereof are also provided. Compared with a CAR-T cell constructed by using FMC63, the CAR-T cell constructed based on the humanized antibody has higher killing effect and tumor removal ability.

16 Claims, 17 Drawing Sheets

Specification includes a Sequence Listing.

(56) References Cited

FOREIGN PATENT DOCUMENTS

| | | | | | |
|---|---|---|---|---|---|
| CN | 109575143 | A | | 4/2019 | |
| CN | 109879966 | A | | 6/2019 | |
| WO | WO-2020224606 | A1 | * | 11/2020 | ......... A61K 40/4211 |
| WO | WO-2021223359 | A1 | * | 11/2021 | ......... A61K 40/4211 |
| WO | WO-2022052913 | A1 | * | 3/2022 | ......... C07K 14/7051 |

OTHER PUBLICATIONS

IRES or 2A In Polycistronic Expression Cassette, VectorBuilder (Year: 2025).*

"Applications and explorations of CRISPR/Cas9 in CAR T-Cell Therapy," Li et al, Briefings in Functional Genomics, 19(3), 2020, 175-182 (Year: 2020).*

* cited by examiner

| | CD19 expression | BCMA expression | Cell type |
|---|---|---|---|
| Nalm6 | + | - | Human acute B lymphocyte leukemia cell |
| Jeko-1 | + | + | Human mantle cell lymphoma leukemia cell |
| RPMI-8226-CD19 | + | + | Human multiple myeloma cell overexpressing CD19 |
| MM.1S | - | + | Human multiple myeloma cell |
| NCI-H929 | - | + | Human multiple myeloma cell |
| RPMI8226 | - | + | Human multiple myeloma cell |

HUMANIZED CD19 ANTIBODY AND USE THEREOF

INCORPORATION OF SEQUENCE LISTING

This application contains a sequence listing submitted in Computer Readable Form (CRF). The CFR file containing the sequence listing entitled "PBA4085875_ST25.txt", which was created on Nov. 4, 2022, and is 29,123 bytes in size. The information in the sequence listing is incorporated herein by reference in its entirety.

TECHNICAL FIELD

The present invention relates to the field of immunotherapy, in particular to a humanized CD19 antibody and use thereof.

BACKGROUND

Antibodies are protective proteins produced by the body under the stimulation of antigens, which are secreted into blood and other body fluids by plasma cells. Antibodies can specifically bind to antigens to neutralize toxins and prevent pathogens invasion. According to the specific binding characteristics of antibodies to antigens, antibody drugs targeting disease-specific biological targets can be developed for the treatment of diseases. Antibody drugs have been applied in the field of anti-tumor and autoimmune treatment, and also play an increasingly important role in the fields of anti viral and bacterial infections, cardiovascular diseases, diabetes, and rare diseases treatment. It is a class of drugs with the highest compound growth rate among current biological drugs.

CD19 is a kind of cluster differentiation antigen, which is an important membrane antigen related to B cell proliferation, differentiation, activation and antibody production. The vast majority of B cell malignant tumors have high expression of CD19 on the surface. Application of T cells modified with chimeric antigen receptor (CAR) in targeting relapsed and refractory B cell malignant tumors expressing CD19 independently developed by multiple centers have achieved unprecedented success. Immunotherapy led by CAR-T has brought hope of "curing cancer" to countless patients.

However, the current immunotherapy still has the problems of high recurrence rate and low safety, and it is necessary to develop more safe and effective immunotherapy methods in this field.

SUMMARY OF THE INVENTION

The purpose of the present invention is to provide a humanized CD19 antibody and use thereof.

In the first aspect of the present invention, it provides a humanized CD19 antibody which comprises an antibody light chain variable region shown in any one of SEQ ID NO: 1-7, and an antibody heavy chain variable region shown in any one of SEQ ID NO: 8-17.

In another preferred embodiment, the antibody comprises an antibody light chain variable region shown in SEQ ID NO: 5 or 6, and an antibody heavy chain variable region shown in any one of SEQ ID NO: 15, 16 or 17.

In another preferred embodiment, the antibody comprises an antibody light chain variable region and an antibody heavy chain variable region selected from the group consisting of:

| Antibody No. | The amino acid sequence of heavy chain variable region | The amino acid sequence of light chain variable region |
|---|---|---|
| VH2 + VL3 | 9 | 3 |
| VH4 + VL3 | 11 | 3 |
| VH2 + VL2 | 9 | 2 |
| VH2 + VL1 | 9 | 1 |
| VH4 + VL1 | 11 | 1 |
| VH4 + VL2 | 11 | 2 |
| VH5 + VL1 | 12 | 1 |
| VH3 + VL2 | 10 | 2 |
| VH3 + VL1 | 10 | 1 |
| VH5 + VL3 | 12 | 3 |
| VH3 + VL3 | 10 | 3 |
| VH5 + VL2 | 12 | 2 |
| VH6 + VL4 | 13 | 4 |
| VH1 + VL2 | 8 | 2 |
| VH1 + VL1 | 8 | 1 |
| VH1 + VL3 | 8 | 3 |
| VH7 + VL6 | 14 | 6 |
| VH8 + VL6 | 15 | 6 |
| VH8 + VL5 | 15 | 5 |
| VH9 + VL5 | 16 | 5 |
| VH10 + VL5 | 17 | 5 |
| VH4 + VL6 | 11 | 6 |
| VH2 + VL6 | 9 | 6 |
| VH2 + VL7 | 9 | 7 |

In another preferred embodiment, the antibody comprises an antibody light chain variable region shown in SEQ ID NO: 5, and an antibody heavy chain variable region shown in SEQ ID NO: 16, or, the antibody comprises an antibody light chain variable region shown in SEQ ID NO: 5, and an antibody heavy chain variable region shown in SEQ ID NO: 17, or, the antibody comprises an antibody light chain variable region shown in SEQ ID NO: 6, and an antibody heavy chain variable region shown in SEQ ID NO: 15.

In another preferred embodiment, the antibody is a double-chain antibody or a single-chain antibody.

In another preferred embodiment, the antibody is a full-length antibody protein or an antigen binding fragment.

In another preferred embodiment, the antibody is a bispecific antibody or a multi-specific antibody.

In another preferred embodiment, the antibody further comprises a linking peptide located between the heavy chain variable region and the light chain variable region.

In another preferred embodiment, the antibody is shown in the following Formula A or B:

$$V_H\text{-}V_L \quad (A);$$

$$V_L\text{-}V_H \quad (B)$$

wherein, $V_H$ is the antibody heavy chain variable region; $V_L$ is the antibody light chain variable region; "—" is a linking peptide or a peptide bond;

preferably has a structure of Formula B.

In another preferred embodiment, the linking peptide is a sequence of 1-4 consecutive SEQ ID NO: 22(GGGGS), preferably 1-4, more preferably 3-4.

In another preferred embodiment, the connection order of the segments in the light chain variable region is: humanized VL FR1-VL CDR1-humanized VL FR2-VL CDR2-humanized VL FR3-VL CDR3-humanized VL FR4;

in another preferred embodiment, the connection order of the segments in the heavy chain variable region is: humanized VH FR1-VH CDR1-humanized VH FR2-VH CDR2-humanized VH FR3-VH CDR3-humanized VH FR4.

In the second aspect of the present invention, it provides a chimeric antigen receptor (CAR) targeting CD19, wherein the antigen binding domain of the CAR is the humanized CD19 antibody according to the first aspect of the present invention.

In another preferred embodiment, the structure of the CAR is shown in the following Formula I:

L-scFv-H-TM-C-CD3ζ (I)

wherein, each "—" is independently a linking peptide or a peptide bond;

L is none or a signal peptide sequence;

scFv is the antigen binding domain targeting CD19;

H is none or a hinge region;

TM is a transmembrane domain;

C is a costimulatory signal molecule;

CD3ζ is a cytoplasmic signaling sequence derived from CD3ζ.

In the third aspect of the present invention, it provides a bispecific CAR targeting CD19 and a first target, wherein, the antigen binding domain targeting CD19 in the bispecific CAR is the humanized CD19 antibody according to the first aspect of the present invention;

and the first target is selected from the group consisting of:

CD2, CD3, CD4, CD5, CD7, CD8, CD19, CD20, CD22, CD25, CD28, CD30,

CD33, CD38, CD40, CD44V6, CD47, CD52, CD56, CD57, CD58, CD79b, CD80,

CD86, CD81, CD123, CD133, CD137, CD151, CD171, CD276, CLL1, B7H4, BCMA, VEGFR-2, EGFR, GPC3, PMSA, CEACAM6, c-Met, EGFRvIII, ErbB2/HER2, ErbB3, HER-2, HER3, ErbB4/HER-4, EphA2, IGF1R, GD2, O-acetyl GD2, O-acetyl GD3, GHRHR, GHR, Flt1, KDR, Flt4, FIt3, CEA, CA125, CTLA-4, GITR, BTLA, TGFBR1, TGFBR2, TGFBR1, IL6R, gp130, Lewis, TNFR1, TNFR2, PD1, PD-L1, PD-L2, PSCA, HVEM, MAGE-A, MSLN, NY-ESO-1, PSMA, RANK, ROR1, TNFRSF4, TWEAK-R, LTPR, LIFRP, LRP5, MUC1, MUC16, TCR α, TCR (3, TLR7, TLR9, PTCH1, WT-1, Robol, Frizzled, OX40, Notch-1-4, APRIL, CS1, MAGE3, Claudin 18.2, Folate receptor α, Folate receptor β, GPC2, CD70, BAFF-R, TROP-2, and a combination thereof.

In another preferred embodiment, the first target is BCMA, and the antigen binding domain (scFv) targeting BCMA in the bispecific CAR comprises an antibody heavy chain variable region shown in SEQ ID NO: 21, and an antibody light chain variable region shown in SEQ ID NO: 20.

In another preferred embodiment, the bispecific CAR comprises both an antigen binding domain targeting the first target and an antigen binding domain targeting CD19.

In another preferred embodiment, the structure of the bispecific CAR is shown in the following Formula II:

L-scFv1-I-scFv2-H-TM-C-CD3ζ (II)

wherein, each "—" is independently a linking peptide or a peptide bond;

L is none or a signal peptide sequence;

I is a flexible linker;

H is none or a hinge region;

TM is a transmembrane domain;

C is a costimulatory signal molecule;

CD3ζ is a cytoplasmic signaling sequence derived from CD3ζ;

one of scFv1 and scFv2 is the antigen binding domain targeting the first target, and the other is the antigen binding domain targeting CD19.

In another preferred embodiment, the scFv1 and scFv2 may be independent, in tandem, or in loop structure.

In another preferred embodiment, the scFv1 is an antigen binding domain targeting the first target, and the scFv2 is an antigen binding domain targeting CD19.

In another preferred embodiment, the scFv1 is an antigen binding domain targeting CD19, and the scFv2 is an antigen binding domain targeting the first target.

In another preferred embodiment, the sequence of the linking peptide comprises a sequence of 1-6, preferably 3-5 consecutive SEQ ID NO: 22(GGGGS).

In another preferred embodiment, the structure of the antigen binding domain targeting the first target is shown in the following Formula C or D:

$V_{L1}$-$V_{H1}$ (C);

$V_{H1}$-$V_{L1}$ (D)

wherein, $V_{L1}$ is the light chain variable region of the anti-first target antibody; $V_{H1}$ is the heavy chain variable region of the anti-first target antibody; "—" is the a linking peptide or a peptide bond.

In another preferred embodiment, the structure of the antigen binding domain targeting BCMA is shown in the following Formula C or D:

$V_{L1}$-$V_{H1}$ (C);

$V_{H1}$-$V_{L1}$ (D)

wherein, $V_{L1}$ is the light chain variable region of the anti-BCMA antibody; $V_{H1}$ is the heavy chain variable region of the anti-BCMA antibody; "—" is the a linking peptide or a peptide bond;

preferably has a structure of Formula D.

In another preferred embodiment, the structure of the antigen binding domain targeting CD19 is shown in the following Formula A or B:

$V_H$-$V_L$ (A);

$V_L$-$V_H$ (B)

wherein, $V_H$ is the antibody heavy chain variable region; $V_L$ is the antibody light chain variable region; "—" is a linking peptide or a peptide bond.

In another preferred embodiment, the scFv1 and/or scFv2 are mouse-derived, human-derived, human-derived and mouse-derived chimeric, or fully humanized single-chain antibody variable region fragments, preferably humanized single-chain antibody variable region fragments.

In another preferred embodiment, the structure of the bispecific CAR is shown in the following Formula III or III':

L-$V_{L3}$-scFv3-$V_{H3}$-H-TM-C-CD3ζ (III)

L-$V_{H3}$-scFv3-$V_{L3}$-H1-TM-C-CD3ζ (III')

wherein, each "—" is independently a linking peptide or a peptide bond;

elements L, H, TM, C and CD3ζ are as described above;

scFv3 is the antigen binding domain targeting CD19, $V_{H3}$ is the heavy chain variable region of the anti-first target antibody, and $V_{L3}$ is the light chain variable region of the anti-first target antibody; or scFv3 is the antigen binding domain targeting the first target, $V_{H3}$ is the heavy chain variable region of anti-CD19 antibody and $V_{L3}$ is the light chain variable region of anti-CD19 antibody.

In another preferred embodiment, the scFv3 is the antigen binding domain targeting BCMA, $V_{H3}$ is the heavy chain variable region of anti-CD19 antibody, and $V_{L3}$ is the light chain variable region of anti-CD19 antibody.

In another preferred embodiment, the antigen binding domain targeting BCMA comprises an antibody heavy chain variable region shown in SEQ ID NO: 21, and an antibody light chain variable region shown in SEQ ID NO: 20.

In another preferred embodiment, the structure of the bispecific CAR is shown in the following Formula III.

In another preferred embodiment, L is a signal peptide selected from the group consisting of CD8, CD28, GM-CSF, CD4, CD137, and a combination thereof.

In another preferred embodiment, L is a signal peptide derived from CD8.

In another preferred embodiment, L has the amino acid sequence as shown in SEQ ID NO: 23.

In another preferred embodiment, H is the hinge region of a protein selected from the group consisting of CD8, CD28, CD137, and a combination thereof.

In another preferred embodiment, H is each independently a CD8-derived hinge region.

In another preferred embodiment, H has the amino acid sequence as shown in SEQ ID NO: 24.

In another preferred embodiment, TM is the transmembrane region of a protein selected from the group consisting of CD28, CD3 epsilon, CD45, CD4, CD5, CD8, CD9, CD16, CD22, CD33, CD37, CD64, CD80, CD86, CD134, CD137, CD154, and a combination thereof.

In another preferred embodiment, TM is each independently a CD8-derived or CD28-derived transmembrane region.

In another preferred embodiment, the CD8-derived transmembrane region has the amino acid sequence as shown in SEQ ID NO: 25.

In another preferred embodiment, the CD28-derived transmembrane region has the amino acid sequence as shown in SEQ ID NO: 26.

In another preferred embodiment, C is a costimulatory signaling molecule of a protein selected from the group consisting of OX40, CD2, CD7, CD27, CD28, CD30, CD40, CD70, CD134, 4-1BB(CD137), PD1, Dap10, CDS, ICAM-1, LFA-1 (CD11a/CD18), ICOS (CD278), NKG2D, GITR, TLR2, and a combination thereof.

In another preferred embodiment, C is a costimulatory signaling molecule derived from CD28 and/or 4-1BB.

In another preferred embodiment, the 4-1BB-derived costimulatory signaling molecule has the amino acid sequence as shown in SEQ ID NO: 27.

In another preferred embodiment, the CD28-derived costimulatory signaling molecule has the amino acid sequence as shown in SEQ ID NO: 28.

In another preferred embodiment, the CD3ζ has the amino acid sequence as shown in SEQ ID NO: 29.

In another preferred embodiment, the CAR (preferably C-terminal or N-terminal) further comprises a cell suicide element.

In another preferred embodiment, the cell suicide element is linked to the L or CD3 of the CAR or the bispecific CAR via T2A.

In the fourth aspect of the present invention, it provides a nucleic acid molecule encoding the humanized CD19 antibody of the first aspect of the present invention, the CAR of the second aspect, or the bispecific CAR of the third aspect of the present invention.

In the fifth aspect of the present invention, it provides a vector comprising the nucleic acid molecule of the fourth aspect of the present invention.

In another preferred embodiment, the vector is selected from the group consisting of DNA, RNA, a plasmid, a lentiviral vector, an adenoviral vector, a retroviral vector, a transposon, and a combination thereof.

In another preferred embodiment, the vector is a lentiviral vector.

In the sixth aspect of the present invention, it provides a host cell comprising the vector of the fifth aspect of the present invention, or having the exogenous nucleic acid molecule of the fourth aspect of the present invention integrated in the chromosome, or expressing the humanized CD19 antibody of the first aspect of the present invention, the CAR of the second aspect of the present invention, or the bispecific CAR of the third aspect of the present invention.

In the sixth aspect of the present invention, it provides an engineered immune cell comprising the vector of the fourth aspect of the present invention, or having the exogenous nucleic acid molecule of the third aspect of the present invention integrated in the chromosome, or expressing the humanized CD19 antibody of the first aspect of the present invention, the CAR of the second aspect of the present invention, or the bispecific CAR of the third aspect of the present invention.

In another preferred embodiment, the immune cell has one or more characteristics selected from the group consisting of:

(a) PD-1 gene expression of the immune cell is silenced;

(b) the immune cell is a T cell, and the TCR gene expression of the T cell is silenced; and (c) the immune cell expresses an exogenous cell suicide element;

(d) the immune cell expresses or secretes PD-1 antibodies, PD-L1 antibodies, CD47 antibodies, Tim3 antibodies, Lag3 antibodies, Tigit antibodies, OX40 antibodies, ICOS antibodies, IL7, CXCL19, IL21, IL15, IL2, IL18, and a combination thereof; and (e) the cytokine-related signaling pathway of the immune cell is enhanced, wherein the cytokine is selected from the group consisting of IL7, CXCL19, IL21, IL15, IL2, IL18, and a combination thereof.

In another preferred embodiment, the engineered immune cell is selected from the group consisting of:

(i) a chimeric antigen receptor T cell (CAR-T cell); or (ii) a chimeric antigen receptor NK cell (CAR-NK cell).

In another preferred embodiment, the immune cell expresses an exogenous cell suicide element.

In another preferred embodiment, the CAR is co-expressed with the cell suicide element in the immune cell.

In another preferred embodiment, the CAR and the cell suicide element are connected by a self-cleaving element.

In another preferred embodiment, the cell suicide element is located at the N-terminal or C-terminal of the CAR.

In another preferred embodiment, the self-cleaving element comprises a 2A sequence or an IRES sequence, preferably P2A and T2A.

In another preferred embodiment, the cell suicide element is selected from the group consisting of HSV-TK, iCasp9, ΔCD20, mTMPK, ΔCD19, RQR8, EGFRt, and a combination thereof.

In another preferred embodiment, the structure of the cell suicide element is shown in the following Formula IV:

L2-D-F (IV)

wherein, each "—" is independently a linking peptide or a peptide bond;

L2 is an optional signal peptide sequence;

D is a suicide switch element;

F is a transmembrane element.

In another preferred embodiment, the signal peptide is a GM-CSFR derived signal peptide.

In another preferred embodiment, the cell suicide element is selected from the group consisting of truncated epidermal growth factor receptor (EGFRt), truncated CD19(CD19t) gene, induced caspase 9 gene (iCasp9), HSV-TK, ACD20, mTMPK, and a combination thereof.

In another preferred embodiment, the cell suicide element is EGFRt.

In another preferred embodiment, the engineered immune cell comprises an universal CAR-T cell.

In another preferred embodiment, the TRAC and B2M genes of the universal CAR-T cell are knocked out.

In the eighth aspect of the present invention, it provides an engineered immune cell, which comprises an exogenous first expression cassette and an exogenous second expression cassette, wherein the first expression cassette is used for expressing a first CAR targeting a first target, and the second expression cassette is used for expressing a second CAR targeting CD19;

or the immune cell expresses the first CAR targeting the first target and the second CAR targeting CD19;

wherein, the antigen binding domain (scFv) targeting CD19 in the second CAR is the humanized CD19 antibody of the first aspect of the present invention;

and the first target is selected from the group consisting of:

CD2, CD3, CD4, CD5, CD7, CD8, CD19, CD20, CD22, CD25, CD28, CD30,

CD33, CD38, CD40, CD44V6, CD47, CD52, CD56, CD57, CD58, CD79b, CD80,

CD86, CD81, CD123, CD133, CD137, CD151, CD171, CD276, CLL1, B7H4, BCMA, VEGFR-2, EGFR, GPC3, PMSA, CEACAM6, c-Met, EGFRvIII, ErbB2/HER2, ErbB3, HER-2, HER3, ErbB4/HER-4, EphA2, IGF1R, GD2, O-acetyl GD 2, O-acetyl GD3, GHRHR, GHR, Flt1, KDR, Flt4, Flt3, CEA, CA125, CTLA-4, GITR, BTLA, TGFBR1, TGFBR2, TGFBR1, IL6R, gp130, Lewis, TNFR1, TNFR2, PD1, PD-L1, PD-L2, PSCA, HVEM, MAGE-A, MSLN, NY-ESO-1, PSMA, RANK, ROR1, TNFRSF4, TWEAK-R, LTPR, LIFRP, LRP5, MUC1, MUC16, TCR α, TCR (3, TLR7, TLR9, PTCH1, WT-1, Robol, Frizzled, OX40, Notch-1-4, APRIL, CS1, MAGE3, Claudin 18.2, Folate receptor α, Folate receptor (3, GPC2, CD70, BAFF-R, TROP-2, and a combination thereof.

In another preferred embodiment, the first target is BCMA, and the antigen binding domain (scFv) targeting BCMA in the first CAR comprises an antibody heavy chain variable region shown in SEQ ID NO: 21, and an antibody light chain variable region shown in SEQ ID NO: 20.

In another preferred embodiment, the second CAR is the CAR of the second aspect of the present invention.

In another preferred embodiment, the first CAR and the second CAR are localized to the cell membrane of the immune cell.

In another preferred embodiment, a first CAR targeting BCMA and a second CAR targeting CD19 are expressed on the cell membrane of the immune cell expresses.

In another preferred embodiment, the first expression cassette and the second expression cassette are located on the same or different vectors.

In another preferred embodiment, the first expression cassette and the second expression cassette are located on the same vector.

In another preferred embodiment, the structure of the first CAR is shown in the following Formula V:

L-scFv1'-H-TM-C-CD3ζ (V)

wherein, each "—" is independently a linking peptide or a peptide bond;

elements L, H, TM, C and CD3 are as described above;

scFv1' is the antigen binding domain targeting BCMA.

In another preferred embodiment, the first CAR and the second CAR are linked via a 2A peptide.

In another preferred embodiment, the sequence of 2A peptide is as shown in SEQ ID NO: 30.

In another preferred embodiment, a cell suicide element is further comprised within the immune cell.

In another preferred embodiment, the cell suicide element and the bispecific CAR are connected (or connected in tandem) via T2A.

In another preferred embodiment, the cell suicide element is connected to the first CAR and/or the second CAR via T2A.

In another preferred embodiment, the PD1 gene expression of the immune cell is silenced.

In another preferred embodiment, the "PD-1 gene expression is silenced" means that the PD-1 gene is not expressed or is low expressed.

In another preferred embodiment, the "low expression" refers to the ratio of the PD-1 gene expression level G1 of the immune cell to the PD-1 gene expression level G0 of the normal immune cell, that is, $G1/G0 \leq 0.5$, preferably $G1/G0 \leq 0.3$, more preferably $\leq 0.2$, more preferably $\leq 0.1$, and most preferably 0.

In another preferred embodiment, the "low expression" refers to the ratio of the PD-1 gene expression level G1 of the CAR-T cell to the PD-1 gene expression level GO of the normal T cell, that is, $G1/G0 \leq 0.5$, preferably $G1/G0 \leq 0.3$, more preferably $\leq 0.2$, more preferably $\leq 0.1$, and most preferably 0.

In the ninth aspect of the present invention, it provides a formulation comprising the humanized CD19 antibody of the first aspect of the present invention, or the engineered immune cell of the seventh or eighth aspects of the present invention, and a pharmaceutically acceptable carrier, diluent or excipient.

In another preferred embodiment, the formulation is a liquid formulation.

In another preferred embodiment, the dosage form of the formulation is an injection.

In another preferred embodiment, the concentration of the engineered immune cells in the formulation is $1\times10^3$-$1\times10^8$ cells/ml, preferably $1\times10^4$-$1\times10^7$ cells/ml.

In the tenth aspect of the present invention, it provides a use of the humanized CD19 antibody of the first aspect of the present invention, or the engineered immune cell of the seventh or eighth aspects of the present invention for the preparation of a medicament or formulation for the prevention and/or treatment of cancer or tumor.

In another preferred embodiment, the tumor is selected from the group consisting of a hematological tumor, a solid tumor, and a combination thereof.

In another preferred embodiment, the hematological tumor is selected from the group consisting of acute myeloid leukemia (AML), multiple myeloma (MM), chronic lymphocytic leukemia (CLL), acute lymphoblastic leukemia (ALL), diffuse large B-cell lymphoma (DLBCL), and a combination thereof.

In another preferred example, the solid tumor is selected from the group consisting of gastric cancer, gastric cancer peritoneal metastasis, liver cancer, kidney tumor, lung cancer, small intestine cancer, bone cancer, prostate cancer, colorectal cancer, breast cancer, colorectal cancer, cervical cancer, ovarian cancer, lymphoma, nasopharyngeal cancer, adrenal tumors, bladder tumors, non-small cell lung cancer (NSCLC), glioma, endometrial cancer, testicular cancer, colorectal cancer, urinary tract tumor, thyroid cancer, and a combination thereof.

In another preferred embodiment, the cancer or tumor is multiple myeloma.

In another preferred embodiment, the cancer or tumor is lymphoma.

In another preferred embodiment, the lymphoma is selected from the group consisting of Hodgkin's lymphoma (HL), diffuse large B-cell lymphoma (DLBCL), follicular lymphoma (FL), chronic lymphocytic leukocyte (CLL), small lymphocytic lymphoma (SLL), marginal zone lymphoma (MZL), mantle cell lymphoma (MCL), Burkitt lymphoma (BL), and other complex B-cell non-Hodgkin's lymphoma.

In another aspect of the present invention, it provides a method for preparing an engineered immune cell, and the engineered immune cell expresses the humanized CD19 antibody of the first aspect of the present invention, the CAR of the second aspect or the bispecific CAR of the third aspect of the present invention, which comprises the following steps:

transferring the nucleic acid molecule of the fourth aspect of the present invention or the vector of the fifth aspect of the present invention into an immune cell to obtain the engineered immune cell.

In another preferred embodiment, the immune cell is a T cell or NK cell.

In the eleventh aspect of the present invention, it provides a method for preparing an engineered immune cell, which comprises the following steps:

(1) providing an immune cell to be modified; and (2) introducing a first expression cassette for expressing the first CAR targeting the first target into the immune cell; and (3) introducing a second expression cassette for expressing the second CAR targeting CD19 into the immune cell; and wherein, the antigen binding domain (scFv) targeting CD19 in the second CAR is the humanized CD19 antibody of the first aspect of the present invention;

and the first target is selected from the group consisting of:

CD2, CD3, CD4, CD5, CD7, CD8, CD19, CD20, CD22, CD25, CD28, CD30,

CD33, CD38, CD40, CD44V6, CD47, CD52, CD56, CD57, CD58, CD79b, CD80,

CD86, CD81, CD123, CD133, CD137, CD151, CD171, CD276, CLL1, B7H4, BCMA, VEGFR-2, EGFR, GPC3, PMSA, CEACAM6, c-Met, EGFRvIII, ErbB2/HER2, ErbB3, HER-2, HER3, ErbB4/HER-4, EphA2, IGF1R, GD2, O-acetyl GD2, O-acetyl GD3, GHRHR, GHR, Flt1, KDR, Flt4, Flt3, CEA, CA125, CTLA-4, GITR, BTLA, TGFBR1, TGFBR2, TGFBR1, IL6R, gp130, Lewis, TNFR1, TNFR2, PD1, PD-L1, PD-L2, PSCA, HVEM, MAGE-A, MSLN, NY-ESO-1, PSMA, RANK, ROR1, TNFRSF4, TWEAK-R, LTPR, LIFRP, LRP5, MUC1, MUC16, TCR α, TCR β, TLR7, TLR9, PTCH1, WT-1, Robol, Frizzled, OX40, Notch-1-4, APRIL, CS1, MAGE3, Claudin 18.2, Folate receptor α, Folate receptor β, GPC2, CD70, BAFF-R, TROP-2, and a combination thereof.

In another preferred embodiment, the step (2) may be performed before, after, simultaneously or alternately with step (3).

In another preferred embodiment, when the immune cell to be modified in step (1) has expressed the first CAR or the second CAR, step (2) or step (3) may be omitted.

In the twelfth aspect of the present invention, it provides a kit for preparing the engineered immune cells of the seventh or eighth aspects of the present invention, and the kit comprises a container, and the nucleic acid molecule of the fourth aspect of the present invention or the vector of the fifth aspect of the present invention located in the container.

In the thirteenth aspect of the present invention, it provides a kit for preparing the engineered immune cells of the seventh or eighth aspect of the present invention, and the kit contains a container, and (1) a first nucleic acid sequence comprising a first expression cassette for expressing a first CAR targeting a first target; and (2) a second nucleic acid sequence comprising a second expression cassette for expressing a second CAR targeting CD19;

located in the container, wherein, the antigen binding domain (scFv) targeting CD19 in the second CAR is the humanized CD19 antibody of the first aspect of the present invention;

and the first target is selected from the group consisting of:

CD2, CD3, CD4, CD5, CD7, CD8, CD19, CD20, CD22, CD25, CD28, CD30,

CD33, CD38, CD40, CD44V6, CD47, CD52, CD56, CD57, CD58, CD79b, CD80, CD86, CD81, CD123, CD133, CD137, CD151, CD171, CD276, CLL1, B7H4, BCMA, VEGFR-2, EGFR, GPC3, PMSA, CEACAM6, c-Met, EGFRvIII, ErbB2/HER2, ErbB3, HER-2, HER3, ErbB4/HER-4, EphA2, IGF1R, GD2, O-acetyl GD2, O-acetyl GD3, GHRHR, GHR, Flt1, KDR, Flt4, Flt3, CEA, CA125, CTLA-4, GITR, BTLA, TGFBR1, TGFBR2, TGFBR1, IL6R, gp130, Lewis, TNFR1, TNFR2, PD1, PD-L1, PD-L2, PSCA, HVEM, MAGE-A, MSLN, NY-ESO-1, PSMA, RANK, ROR1, TNFRSF4, TWEAK-R, LTPR, LIFRP, LRP5, MUC1, MUC16, TCR α, TCR β, TLR7, TLR9, PTCH1, WT-1, Robol, Frizzled, OX40, Notch-1-4, APRIL, CS1, MAGE3, Claudin 18.2, Folate receptor α, Folate receptor β, GPC2, CD70, BAFF-R, TROP-2, and a combination thereof.

In another preferred embodiment, the first and second nucleic acid sequences are located in the same or different containers.

In another preferred embodiment, the first and second nucleic acid sequences are located in the same expression vector.

In the fourteenth aspect of the present invention, it provides a use of the engineered immune cell of the seventh or eighth aspect of the present invention for the prevention and/or treatment of cancer or tumor.

In another preferred embodiment, the cancer or tumor is multiple myeloma, hematologic tumor, or lymphoma.

In the fifteenth aspect of the present invention, it provides a method of treating a disease comprising administering to a subject in need of treatment an appropriate amount of the cells of the seventh or eighth aspect of the present invention, or the formulation of the sixth aspect of the present invention.

In another preferred embodiment, the disease is cancer or tumor.

It should be understood that within the scope of the present invention, each technical features of the present invention described above and in the following (as examples) may be combined with each other to form a new or preferred technical solution, which is not listed here due to space limitations.

Figure 1:
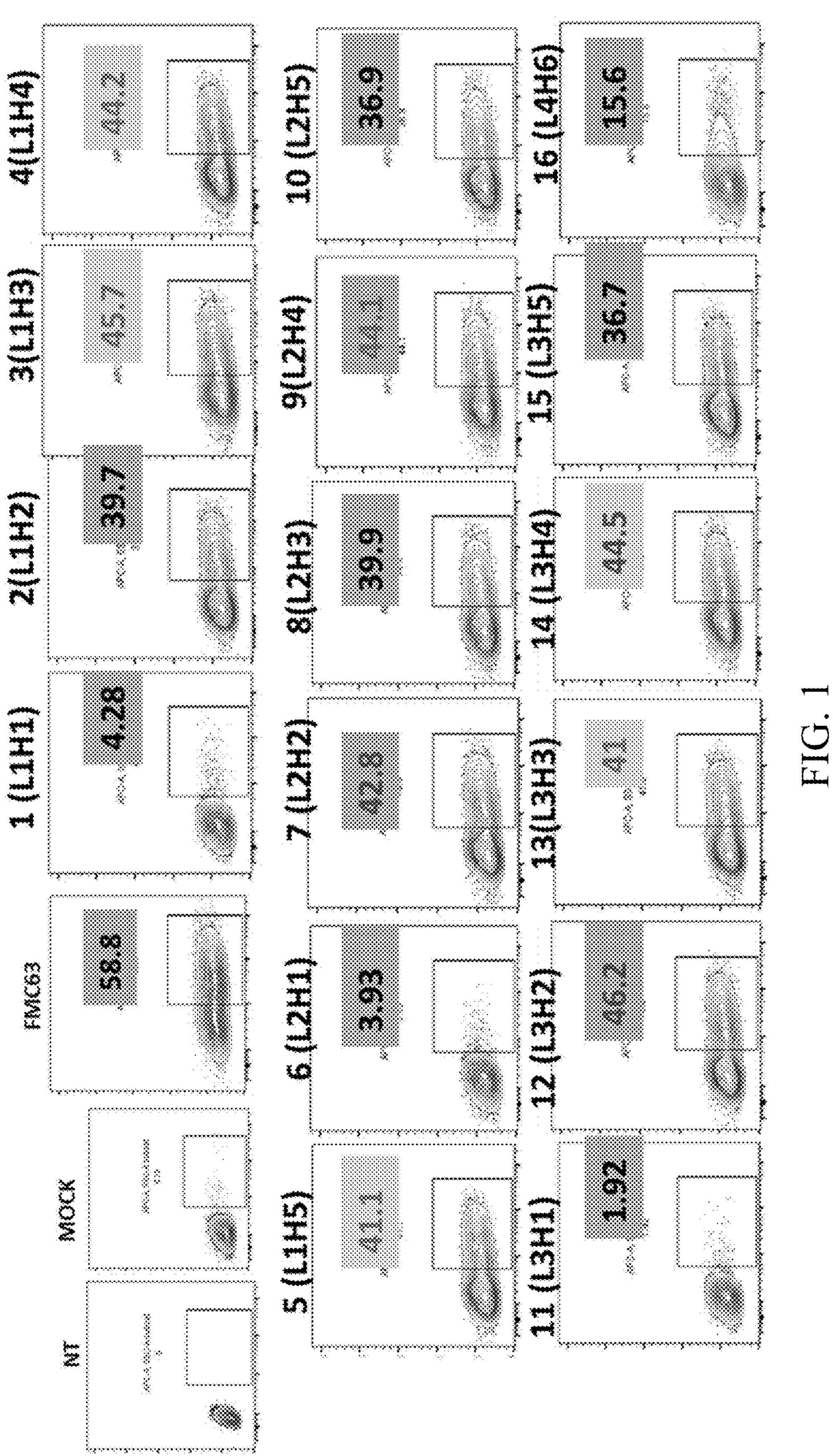
FIG. 1 shows the CAR expression of CAR-T cells modified with FMC63 and humanized FMC63 antibody scFv.

Wherein, LmHn or HnLm (m or n is a positive integer) represents a CAR-T cell constructed with humanized antibodies with VLm and VHn. In the specific structure of CAR, VL is in the front and VH is in the back. Except for FIG. 4, FMC63 in each figure represents CAR-T cells constructed by using FMC63. In each figure, NT represents untreated T cells.

DETAILED DESCRIPTION

After extensive and in-depth research, the inventors has constructed a new humanized CD19 antibody for the first time, which is obtained based on FMC63 chimeric antibody for humanization. The present invention also provides CAR-T cells and dual CAR-T cells constructed based on the humanized antibody and related applications. Compared with the CAR-T cells constructed by FMC63, the CAR-T cells and dual CAR-T cells constructed by the present invention have higher killing effect and tumor elimination ability. The present invention has been completed on this basis.

Term

In order to make this disclosure easier to understand, certain terms are first defined. As used in this application, unless expressly provided herein, each of the following terms shall have the meanings given below. Other definitions are set out throughout the application.

The term "about" may refer to a value or composition within the acceptable error range of a particular value or composition as determined by those skilled in the art, which will depend in part on how the value or composition is measured or determined.

The term "administration" refers to the physical introduction of a product of the present invention into a subject using any of a variety of methods and delivery systems known to those skilled in the art, including intravenous, intramuscular, subcutaneous, intraperitoneal, spinal or other parenteral routes of administration, such as by injection or infusion.

It should be understood that the amino acid names herein adopt the internationally accepted single-English letter identification, and the corresponding amino acid names are abbreviated in three English letters: Ala (A), Arg(R), Asn (N), Asp(D), Cys(C), Gln(Q), Glu(E), Gly(G), His(H), I1e (I), Leu(L), Lys(K), Met(M), Phe(F), Pro(P), Ser(S), Thr (T), Trp(W), Tyr(Y), Val(V).

CD19

CD19 molecule is a transmembrane protein on the surface of B cells, which is closely related to B cell activation, signal transduction and growth regulation. CD19 is expressed on the surface of almost all B cells. CAR-T cells targeting CD19 are currently effective in the treatment of leukemia and lymphoma. CD19 can also be used to treat multiple myeloma.

B Cell Maturation Antigen (BCMA)

BCMA is a transmembrane protein, which is expressed on the surface of mature B lymphocytes, namely plasmablasts and plasma cells. Multiple myeloma is caused by abnormal proliferation of plasma cells and invasion of bone marrow. Studies have shown that BCMA is expressed on multiple myeloma cells. Car-T cells targeting BCMA have been proved to be able to specifically kill myeloma cells. However, some patients will still have a relapse process after receiving BCMA-targeted CAR-T cell therapy. For these patients with recurrence, it is necessary to find a target different from BCMA in order to continue treatment.

Antibody

As used herein, the term "antibody" or "immunoglobulin" is a heterotetrameric glycoprotein of about 150,000 Da having the same structural characteristics, which consists of two identical light chains (L) and two identical heavy chains (H). Each light chain is linked to a heavy chain via a covalent disulfide bond, and different immunoglobulin isotypes have different numbers of disulfide bonds between the heavy chains. There are also regularly spaced intrachain disulfide bonds in each heavy and each light chain. Each heavy chain has a variable region (VH) at one end, followed by a plurality of constant regions. Each light chain has a variable region (VL) at one end and a constant region at the other end; the constant region of light chain pairs with the first constant region of heavy chain, and the variable region of light chain pairs with the variable region of heavy chain. Special amino acid residues form an interface between the variable regions of a light chain and a heavy chain.

As used herein, the term "variable" means that certain portion of the variable region in an antibody differ in sequence, which is responsible for the binding and specificity of various specific antibodies to their specific antigen. However, the variability is not distributed evenly throughout the variable regions of an antibody. It is concentrated in three fragments called complementarity determination regions (CDRs) or hypervariable regions in light chain and heavy chain variable regions. The conserved parts of variable regions are called framework regions (FRs). Each of the variable regions of naturally occurring heavy and light chains comprises four FR regions, which are generally in a β-sheet configuration, joined by the three CDRs forming a linking loop, and in some cases, may form a partial β-sheet structure. The CDRs in each chain are closely linked together via the FR regions, and together with the CDRs of the other chain, form the antigen binding site of an antibody (see Kabat et al., NIH Publ. No. 91-3242, Volume I, pages 647-669 (1991)). Constant regions are not directly involved in the binding of antibodies to antigen, however, they exhibit different effector functions, such as participating in the antibody-dependent cytotoxicity of antibodies.

The "light chain" of vertebrate antibodies (immunoglobulins) can be classified into one of two significantly different categories (called κ and λ) according to the amino acid sequence of its constant region. According to the amino acid sequence of its heavy chain constant region, immunoglobulins can be divided into different types. There are mainly 5 types of immunoglobulins: IgA, IgD, IgE, IgG and IgM, some of which can be further divided into subtypes (isotype), such as IgG1, IgG2, IgG3, IgG4, IgA and IgA2. The heavy chain constant regions corresponding to different types of immunoglobulins are called α, δ, ε, γ, and μ. The subunit structure and three-dimensional configuration of different classes of immunoglobulins are well known to those in the art.

In general, the antigen binding characteristics of an antibody can be described by three specific regions located in the heavy chain and light chain variable regions, called the variable regions (CDRs), which separate this segment into four frame regions (FRs). The amino acid sequences of the four FRs are relatively conservative and do not directly participate in the binding reaction. These CDRs form a loop structure, and the β-sheets formed by the FRs in between are spatially close to each other. The CDRs on the heavy chain and the CDRs on the corresponding light chain constitute the antigen-binding site of the antibody. It can be determined which amino acids constitute the FR or CDR region by comparing the amino acid sequences of antibodies of the same type.

The present invention includes not only intact antibodies, but also fragments of immunologically active antibodies or fusion proteins formed by antibodies with other sequences. Thus, the present invention also includes fragments, derivatives and analogs of the antibody.

In the present invention, the antibodies include murine, chimeric, humanized or full-human antibodies prepared with techniques well known to those skilled in the art. Recombinant antibodies, such as chimeric and humanized monoclonal antibodies, including human and non-human parts, can be obtained by standard DNA recombination techniques, and they are all useful antibodies. A chimeric antibody is a molecule in which different portions are derived from different animal species, such as a chimeric antibody having variable regions of a monoclonal antibody from a mouse, and constant regions from a human immunoglobulin (see, for example, U.S. Pat. Nos. 4,816,567 and 4,816,397, which are hereby incorporated by reference in their entirety). Humanized antibodies refer to antibody molecules derived from non-human species, having one or more complementary determining regions (CDRs) derived from non-human species and framework regions derived from human immunoglobulin molecules (see U.S. Pat. No. 5,585,089, which is hereby incorporated by reference in its entirety). These chimeric and humanized monoclonal antibodies can be prepared using DNA recombination techniques well known in the art.

In the present invention, the antibody may be monospecific, bispecific, trispecific, or with more multiple specificities.

In the present invention, the antibody of the present invention further includes a conservative variant thereof, which means a polypeptide formed by replacing at most 10, preferably at most 8, more preferably at most 5, and most preferably at most 3 amino acids with amino acid of similar properties as compared with the amino acid sequence of the antibody of the present invention. These conservative variant polypeptides are best produced by amino acid substitution according to Table A.

TABLE A

| Initial residue | Representative substitution | Preferred substitution |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

Chimeric Antigen Receptor (CAR)

The chimeric antigen receptor (CAR) of the present invention includes an extracellular domain, a transmembrane domain, and an intracellular domain. The extracellular domain includes a target-specific binding element (also called antigen binding domain). The intracellular domain includes a costimulatory signal transduction region and a zeta chain part. The costimulatory signal transduction region refers to a part of intracellular domain including costimulatory molecules. The costimulatory molecules are the cell surface molecules needed for the effective response of lymphocytes to antigens, not antigen receptors or their ligands.

The linker may be incorporated between the extracellular and transmembrane domains of the CAR, or between the cytoplasmic and transmembrane domains of the CAR. As used herein, the term "linker" generally refers to any oligopeptide or polypeptide that plays the role of connecting the transmembrane domain to the extracellular domain or cytoplasmic domain of the polypeptide chain. The linker may comprise 0 to 300 amino acids, preferably 2 to 100 amino acids and most preferably 3 to 50 amino acids.

In a preferred embodiment of the present invention, the extracellular domain of the CAR provided by the present invention comprises an antigen binding domain targeting CD19. The CAR of the present invention, when expressed in T cells, is capable of antigen recognition based on antigen binding specificity. When it binds to its associated antigen, it affects tumor cells, causing tumor cells to not grow, be killed or be affected in other ways, and leading to the reduction or elimination of tumor burden of the patient. The antigen binding domain is preferably fused with an intracellular domain from one or more of the costimulatory molecules and the zeta chain. Preferably, the antigen binding domain is fused with an intracellular domain of the combination of the 4-1BB signaling domain and the CD3 zeta signaling domain.

As used herein, "antigen-binding domain" and "single-chain antibody fragment" each refers to a Fab fragment, a Fab' fragment, a F $(AB')_2$ fragment, or a single Fv fragment with antigen-binding activity. Fv antibody contains antibody heavy chain variable region and light chain variable region, but no constant region, and has the smallest antibody fragment of all antigen binding sites. In general, Fv antibody further contains a polypeptide linker between the VH and VL domains and is capable of forming the structure required for antigen binding. The antigen binding domain is usually a scFv (single-chain variable fragment). The size of scFv is generally ⅙ of that of an intact antibody. The single-chain antibody is preferably an amino acid chain sequence encoded by a nucleotide chain. As a preferred embodiment of the present invention, the antigen binding domain comprises an antibody that specifically recognizes CD19. Optionally, the antigen binding domain further comprises an antibody that specifically recognizes BCMA, preferably a single chain antibody.

For the hinge region and the transmembrane region (transmembrane domain), the CAR may be designed to include the transmembrane domain fused to the extracellular domain of the CAR. In one embodiment, a transmembrane domain naturally associated with one of the domains in the CAR is used. In some examples, the transmembrane domain may be selected, or modified by amino acid substitution, to avoid binding such domains to transmembrane domains of the same or different surface membrane proteins, thereby minimizing interaction with other members of the receptor complex.

The intracellular domain in the CAR of the present invention includes the signal transduction domain of 4-1BB and the signal transduction domain of CD3.

Preferably, the CAR of the present invention further comprises a cell suicide element.

Preferably, the scFv targeting CD19 of the present invention comprises an antibody light chain variable region shown in any one of SEQ ID NOs: 1-7, and an antibody heavy chain variable region shown in any one of SEQ ID NOs: 8-17.

Bispecific CAR

CD19 is a glycoprotein with a molecular weight of 95 kDa. It is expressed on the membrane surface of pre-B cells and mature B cells. It is closely related to the Ca++ transmembrane transduction pathway of B cells and has a regulatory effect on the proliferation and differentiation of B cells. CD19 is mainly expressed in normal B cells and cancerous B cells, with high tissue expression specificity, and is a good antibody or CAR-T immunotherapy target. However, in the process of immunotherapy, the loss of CD19 epitope of B cells often occurs, causing patients to have no response to immunotherapy or relapse.

Bispecific means that the same CAR can specifically bind and immunologically recognize two different antigens. CAR can produce immune response by binding any antigen.

The present invention provides a bispecific CAR targeting CD19 and another tumor target, as described in the third aspect of the present invention.

In another preferred embodiment, the bispecific CAR targets CD19 and BCMA.

In a preferred embodiment of the present invention, the extracellular domain of CAR provided by the present invention comprises the antigen binding domain targeting CD19 and BCMA, including anti-CD19 scFv and anti-BCMA scFv.

In another preferred embodiment, the present invention provides a bispecific chimeric antigen receptor for CD19 and BCMA antigens. The CAR structural components that simultaneously target CD19 and BCMA may include a signal peptide, a scFv against CD19, a scFv against BCMA, a hinge region, a transmembrane region, and an intracellular T cell signaling region, wherein the CD19 scFv and BCMA scFv are linked by a short peptide segment (G4S)×N. The structure of the CAR that simultaneously targets CD19 and BCMA is as described in the third aspect of the present invention.

In another preferred embodiment, the CD19 and BCMA bispecific CAR of the present invention is a single structure, comprising the scFv against CD19 and BCMA. Among them, CAR contains CD19 scFv and BCMA scFv, and the order of CD19 scFv and BCMA scFv and the hinge are the main influencing factors of its function.

The present invention uses the CAR bidirectional targeting CD19 and BCMA, which has significantly enhanced affinity, significantly increase the activity of immune cells, and has a synergistic effect, compared with the CAR targeting single antigen. In addition, due to the uneven expression levels of CD19 and BCMA in tumor cells, dual-targeted CAR-T therapy has a wider range. CAR-immune cells targeting CD19 and BCMA at the same time can reduce the possibility of antigen escape caused by down-regulation or deletion of a single surface antigen.

In a preferred embodiment of the present invention, the present invention uses humanized CD19 scFv to construct a bispecific CAR, which can further improve the killing effect and tumor elimination ability.

Chimeric Antigen Receptor T Cells (CAR-T Cells)

As used herein, the terms "CAR-T cell", "CAR-T", "CAR-T cell of the present invention" include CAR-T cells incorporated in the third aspect of the present invention.

Compared with other T cell-based treatment methods, CAR-T cells have the following advantages: (1) the action process of CAR-T cells is not restricted by MHC; (2) since many tumor cells express the same tumor antigen, once the gene construction of the CAR for a certain tumor antigen is completed, it can be widely used; (3) CAR can use both tumor protein antigens and glycolipid non-protein antigens, and expands the target range of tumor antigens; (4) the risk of rejection is reduced by using autologous cells of patient; (5) CAR-T cells have immune memory function and can survive in vivo for a long time.

The present invention provides a bispecific CAR-T cell comprising a CAR targeting CD19 and a CAR targeting another tumor target, as described in the eighth aspect of the present invention.

In another preferred embodiment, the another tumor target is BCMA.

In a preferred embodiment of the present invention, the present invention uses humanized CD19 scFv to construct a bispecific CAR-T cells, which can further improve the killing effect and tumor elimination ability.

Chimeric Antigen Receptor NK Cells (CAR-NK Cells)

As used herein, the terms "CAR-NK cell", "CAR-NK" and "CAR-NK cell of the present invention" all refer to CAR-NK cells included in the third aspect of the present invention. The CAR-NK cells of the present invention can be used to treat tumors with high expression of CD19, such as multiple myeloma, lymphoma, etc.

Natural killer (NK) cells are a major type of immune effector cells, which protect the body from virus infection and tumor cell invasion through non-antigen-specific pathways. NK cells may acquire new functions by engineering (genetically modified), including the ability to specifically recognize tumor antigens and have enhanced anti-tumor cytotoxicity.

Compared with autologous CAR-T cells, CAR-NK cells further have the following advantages, such as: (1) they directly kill tumor cells by releasing perforin and granzyme, but have no killing effect on normal cells of the body; (2) they release a very small amount of cytokines so that reduce the risk of cytokine storms; (3) they are easy to be expanded and developed into "ready-made" products in vitro. In addition, it is similar to CAR-T cell therapy.

Suicide Gene Switch

In order to further control the defects such as non-tumor targeting of CAR-T cells and cytokine release syndrome, the CART cells in the present invention are all equipped with a suicide gene switch, which can effectively remove CAR-T cells in the body and block unknown or uncontrollable long-term toxicity under the function of exogenous drugs to ensure the safety of patients.

The suicide switch used in the present invention may be herpes simplex virus thymidine kinase (HSV-TK), inducible caspase 9 (iCasp9), CD20, mutated human thymidylate kinase (mTMPK), etc. Comparatively speaking, HSV-TK, iCasp9 and CD20 have the same ability to remove CAR-cells, but the clearance speed of iCasp9 and CD20 is faster and the clearance speed of HSV-TK is slower.

The iCasp9 suicide switch contains a FKBP12-F36V domain, which can be connected by a flexible linker to cysteine aspartate proteinase 9, which does not contain a recruitment domain. The FKBP12-F36V contains an FKBP domain, wherein phenylalanine replaces valine at the 36th amino acid residue site. It has high selectivity and subnanomolar affinity, and can combine dimeric synthetic ligands, such as other inert small molecules AP1903. When small molecules are added, they can promote its dimerization, thus inducing cell apoptosis, which is ineffective for normal cells without suicide switch.

The induction safety switch caspase9 (iCasp9) uses human caspase9 to fuse FK506 binding protein (FKBP), which can be induced to form dimer with chemical inducer (AP1903/Rimiduid, Bellicum Pharmaceutical), leading to apoptosis of cells expressing the fusion protein.

Although CD19 and BCMA are highly expressed in tumor cells, they are also expressed in normal B cells, and the engineered immune cells of the present invention attack normal B cells in vivo.

How to control the safety of CAR-cells has always been an urgent problem to be solved. Adding a safety switch to a CAR-cell is the safest way to terminate CAR-cell activity. The inducible iCasp9 safety switch controls CAR-cell clearance after the CAR-cell produces severe toxicity (CRS/neurotoxicity) or after the patient achieves long-term sustained remission.

Vector

The nucleic acid sequence encoding the desired molecule may be obtained using recombination methods known in the art, such as, for example, by screening a library from cells expressing the gene, by deriving the gene from a vector known to include the gene, or by direct isolation from cells and tissues containing the gene using standard techniques. Optionally, the gene of interest may be synthesized and produced.

The present invention also provides a vector in which the expression cassette of the present invention is inserted. Vectors derived from retroviruses such as lentiviruses are suitable tools for long-term gene transfer because they allow long-term, stable integration of transgenes and their proliferation in daughter cells. Lentiviral vectors have advantages over vectors derived from carcinogenic retroviruses such as murine leukemia viruses because they can transduce non-proliferative cells, such as hepatocytes. They also have the advantage of low immunogenicity.

In brief summary, the expression cassette or nucleic acid sequence of the present invention is usually operably linked to the promoter and incorporated into the expression vector.

The vector is suitable for replication and integration of eukaryotic cells. A typical cloning vector contains a transcription and translation terminator, an initial sequence, and a promoter that can be used to regulate expression of the desired nucleic acid sequences.

The expression construct of the present invention can also be used for nucleic acid immunization and gene therapy by using the standard gene delivery scheme. Methods of gene delivery are known in the art. See, for example, U.S. Pat. Nos. 5,399,346, 5,580,859, 5,589,466, which are incorporated herein by reference in their entirety. In another embodiment, the present invention provides a gene therapy vector.

The nucleic acid can be cloned into many types of vectors. For example, the nucleic acid may be cloned into such vectors, including, but not limited to, plasmids, phage particles, phage derivatives, animal viruses, and cosmid. Specific vectors of interest include expression vectors, replication vectors, probe generation vectors, and sequencing vectors.

Further, the expression vector may be provided to the cell in the form of a viral vector. Viral vector technology is well known in the art and is described in, for example, Sambrook et al. (2001, Molecular Cloning: A Laboratory Manual, Cold Spring Harbor Laboratory, New York) and other manuals of virology and molecular biology. Viruses that may be used as vectors include, but are not limited to, retroviruses, adenoviruses, adeno-associated viruses, herpes viruses, and lentiviruses. Typically, a suitable vector comprises a replication origin, a promoter sequence, a convenient restriction enzyme site, and one or more selectable markers (e.g., WO01/96584; WO01/29058; and U.S. Pat. No. 6,326,193) operative in at least one organism.

A number of virus-based systems have been developed for the transfer of genes into mammalian cells. For example, retroviruses provide a convenient platform for gene delivery systems. Selected genes can be inserted into vectors and packaged into retroviral particles using techniques known in the art. The recombinant virus can then be isolated and delivered to the subject cells in vivo or ex vivo. Many retroviral systems are known in the art. In some embodiments, an adenoviral vector is used. Many adenoviral vectors are known in the art. In one embodiment, a lentiviral vector is used.

Additional promoter elements, such as enhancers, can regulate the frequency of transcription initiation. Typically, these are located in the 30-110 bp region upstream of the start site, although it has recently been shown that many promoters also contain functional elements downstream of the start site. The spacing between promoter elements is often flexible so that when the element is inverted or moved relative to the other, the promoter function is maintained. In the thymidine kinase (tk) promoter, the separation between the promoter elements can be increased by 50 bp, before the activity begins to decline. Depending on the promoter, it is shown that a single element can act cooperatively or independently to initiate transcription.

An example of a suitable promoter is the immediate early cytomegalovirus (CMV) promoter sequence. The promoter sequence is a strongly constitutive promoter sequence capable of driving high-level expression of any polynucleotide sequence operably linked to it. Another example of a suitable promoter is the elongation growth factor-1 α(EF-1α). However, other constitutive promoter sequences can also be used, including but not limited to early promoter of simian virus 40 (SV40), mouse breast cancer virus (MMTV), human immunodeficiency virus (HIV) long-terminal repeat (LTR) promoter, MoMuLV promoter, avian leukemia virus promoter, immediate early promoter of Epstein-Barr virus, Rous's sarcoma virus promoter, and human gene promoter, such as, but not limited to, an actin promoter, a myosin promoter, a heme promoter, and a creatine kinase promoter. Further, the present invention should not be limited to the use of constitutive promoters. Inducible promoters are also considered as part of the present invention. The use of inducible promoters provides a molecular switch that can turn on expression of a polynucleotide sequence operably linked to an inducible promoter when such expression is desired, or turn off expression when the expression is undesirable. Examples of inducible promoters include, but are not limited to, metallothionein promoters, glucocorticoid promoters, progesterone promoters, and tetracycline promoters.

In order to evaluate the expression of the CAR polypeptide or part thereof, the expression vector introduced into the cell may also contain either or both of the selectable marker genes or reporter genes in order to identify and select the expression cells from the cell population seeking to be transfected or infected by the viral vector. In other respects, selectable markers can be carried on a single piece of DNA and used in co-transfection procedures. Both selectable markers and reporter genes can be flanked with appropriate regulatory sequences to be able to be expressed in host cells. Useful selectable markers include, for example, antibiotic resistance genes, such as neo, etc.

Reporter genes are used to identify potentially transfected cells and to evaluate the functionality of regulatory sequences. Typically, the reporter gene is the following gene: it is not present in or expressed by the recipient organism or tissue, and it encodes a polypeptide, the expression of which is clearly represented by some easily detectable properties such as enzyme activity. After DNA has been introduced into the receptor cells, the expression of the reporter gene is determined at the right time. Suitable reporter genes may include genes encoding luciferase, β-galactosidase, chloramphenicol acetyltransferase, secretory alkaline phosphatase, or green fluorescent protein (e.g., Ui-Tei et al., 2000FEBS Letters 479:79-82). Suitable expression systems are well known and can be prepared using known techniques or commercially available. In general, a construct with a minimum of 5 flanking regions that show the highest level of reporter expression are identified as a promoter. Such promoter region can be linked to a reporter gene and used to evaluate the ability of a reagent to regulate promoter-driven transcription.

Methods of introducing genes into cells and expressing genes into cells are known in the art. In the content of the expression vector, the vector can be easily introduced into the host cell by any method in the art, for example, mammalian, bacterial, yeast or insect cells. For example, the expression vector can be transferred into the host cell by physical, chemical or biological means.

Physical methods for introducing polynucleotides into host cells include calcium phosphate precipitation, lipid transfection, particle bombardment, microinjection, electroporation, etc. Methods of producing cells including vectors and/or exogenous nucleic acids are well known in the art. See, for example, Sambrook, etc. (2001, Molecular Cloning: A Laboratory Manual, Cold Spring Harbor Laboratory, New York). The preferred method for introducing polynucleotides into host cells is calcium phosphate transfection.

Biological methods of introducing polynucleotides of interest into host cells include the use of DNA and RNA vectors. Viral vectors, especially retroviral vectors, have become the most widely used method for inserting genes into mammalian cells such as human cells. Other viral vectors may be derived from lentivirus, poxvirus, herpes simplex virus I, adenovirus and adeno-associated virus, etc. See, for example, U.S. Pat. Nos. 5,350,674 and 5,585,362.

Chemical means of introducing polynucleotides into host cells include colloidal dispersion systems, such as macromolecular complexes, nanocapsules, microspheres, beads; and lipid-based systems, including oil-in-water emulsions, micelles, mixed micelles, and liposomes. An exemplary colloidal system used as an in vitro and in vivo delivery vehicle is a liposome (e.g., an artificial membrane capsule).

In the case of using a non-viral delivery system, the exemplary delivery tool is liposome. Lipid preparations are consider to be used to introduce nucleic acids into host cells (in vitro, ex vivo or in vivo). In another aspect, the nucleic acid may be associated with lipids. The nucleic acid associated with lipids may be encapsulated into the aqueous interior of the liposome, scattered in the lipid bilayer of the liposome, attached to the liposome by a connecting molecule associated with both the liposome and the oligonucleotide, trapped in the liposome, complexed with the liposome, dispersed in a solution containing the lipid, mixed with the lipid, combined with the lipid, contained in the lipid as a suspension, contained in the micelle or complexed with the micelle, or otherwise associated with lipids. Lipids, lipid/DNA or lipid/expression vectors associated with the composition are not limited to any specific structure in solution. For example, they may exist in bilayer structures as micelles or have “collapsed” structures. They may also be simply dispersed in solution, possibly forming aggregates of uneven size or shape. Lipids are fatty substances, which may be naturally occurring or synthesized lipids. For example, lipids include fat droplets that occur naturally in the cytoplasm and in compounds containing long-chain aliphatic hydrocarbons and their derivatives, such as fatty acids, alcohols, amines, amino alcohols and aldehydes.

In a preferred embodiment of the present invention, the vector is a lentiviral vector.

Formulation

The present invention provides a formulation comprising the CAR-T cells of the first aspect of the present invention, and a pharmaceutically acceptable carrier, diluent or excipient. In one embodiment, the formulation is a liquid formulation. Preferably, the formulation is an injection. Preferably, the concentration of the CAR-T cells in the formulation is $1\times10^3$-$1\times10^8$ cells/ml, more preferably $1\times10^4$-$1\times10^7$ cells/ml.

In one embodiment, the formulation may include buffers such as neutral buffered saline, sulfate buffered saline, etc.; carbohydrates such as glucose, mannose, sucrose or glucan, mannitol; proteins; polypeptides or amino acids such as glycine; antioxidants; chelating agents such as EDTA or glutathione; adjuvants (e.g., aluminum hydroxide); and preservatives. The formulations of the present invention are preferably formulated for intravenous administration.

Therapeutic Use

The present invention includes therapeutic use of cells (e.g., T cells) transduced with a lentiviral vector (LV) encoding the expression cassette of the present invention. Transduced T cells can target tumor cell markers CD19 or CD19 and BCMA, synergistically activate T cells and cause T cell immune response, thus significantly improving the killing efficiency on tumor cells.

Accordingly, the present invention also provides a method of stimulating a T cell-mediated immune response to a target cell population or tissue of a mammal comprising the step of administering to a mammal the CAR-T cells of the present invention.

In one embodiment, the present invention includes a type of cell therapy in which autologous T cells (or heterologous donors) from a patient are isolated, activated and genetically modified to produce CAR-T cells, and subsequently injected into the same patient. In this way, the probability of graft-versus-host disease is extremely low, and the antigen is recognized by T cells in a manner without MHC restriction. In addition, one kind of CAR-T can treat all cancers that express the antigen. Unlike antibody therapy, CAR-T cells can replicate in vivo, resulting in long-term persistence that can lead to sustained tumor control.

In one embodiment, the CAR-T cells of the present invention can undergo stable in vivo T cell expansion and can last an extended amount of time. In addition, the CAR-mediated immune response can be part of an adoptive immunotherapy step in which CAR-modified T cells induce an immune response specific to the antigen-binding domain in the CAR. For example, anti-BCMA and/or CD19 CAR-T cells elicit a specific immune response against BCMA and/or CD19-expressing cells.

Although the data disclosed herein specifically discloses lentiviral vectors including an anti-CD19 scFv or anti-CD19 and BCMA scFv, a hinge and a transmembrane region, and a 4-1BB/CD28 and CD3 zeta signaling domain, the present invention should be interpreted to include any number of changes to each of the construct components.

Treatable cancers include tumors that have not been vascularized or have basically not been vascularized, and tumors that have been vascularized. The cancers may include non-solid tumors (such as hematological tumors, such as leukemia and lymphoma) or may include solid tumors. The types of cancer treated with the CAR of the present invention include, but are not limited to, carcinomas, blastocytomas, and sarcomas, and certain leukemic or lymphoid malignancies, benign and malignant tumors, and malignant tumors, such as sarcomas, carcinomas, and melanoma. It also includes adult tumors/cancers and pediatric tumors/cancers.

Hematological cancers are cancers of the blood or bone marrow. Examples of hematologic (or haematogenic) cancers include leukemia, including acute leukemia (such as acute lymphocytic leukemia, acute myeloid leukemia, acute myelogenous leukemia and myeloblastic, premyelocytic, granulo-monocytic, monocytic and erythroleukemia), chronic leukemia (such as chronic myeloid (granulocytic) leukemia, chronic myelogenous leukemia and chronic lymphocytic leukemia), polycythemia vera, lymphoma, Hodgkin’s disease, non-Hodgkin’s lymphoma (painless and high-grade forms)), multiple myeloma, Waldenstrom’s macroglobulinemia, heavy chain disease, myelodysplastic syndrome, hairy cell leukemia and spinal cord dysplasia.

A solid tumor is an abnormal mass of tissue that usually does not contain a cyst or fluid area. A solid tumor may be benign or malignant. Different types of solid tumors are named after the cell types that form them (such as sarcomas, carcinomas, and lymphomas). Examples of solid tumors such as sarcoma and cancer include fibrosarcoma, mucinous sarcoma, liposarcoma mesothelioma, lymphoid malignant tumor, pancreatic cancer and ovarian cancer.

The CAR-modified T cells of the present invention can also be used as a vaccine type for ex vivo immunization and/or in vivo therapy of mammals. Preferably, the mammal is a human.

For ex vivo immunization, at least one of the following occurs in vitro before the cells are administered into mammals: i) expanding the cells, ii) introducing the nucleic acid encoding CAR into the cells, and/or iii) cryopreservation of the cells.

The ex vivo procedure is well known in the art and is discussed more fully below. In brief, cells are isolated from mammals (preferably humans) and genetically modified (i.e., transduced or transfected in vitro) with a vector expressing the CAR disclosed herein. CAR-modified cells can be administered to mammalian recipients to provide therapeutic benefits. The mammalian recipient may be human, and CAR-modified cells may be autologous relative to the recipient. Optionally, the cells may be allogeneic, syngeneic or xenogeneic relative to the recipient.

In addition to the use of cell-based vaccines in terms of ex vivo immunization, the present invention also provides compositions and methods for in vivo immunization to induce an immune response against an antigen in a patient.

The present invention provides a method of treating a tumor comprising administering to a subject in need thereof a therapeutically effective amount of the CAR-modified T cells of the present invention.

The CAR-modified T cells of the present invention may be administered alone or as a pharmaceutical composition in combination with a diluent and/or with other components such as IL-2, IL-17 or other cytokines or cell populations. Briefly, the pharmaceutical composition of the present invention may comprise a population of target cells as described herein in combination with one or more pharmaceutically or physiologically acceptable carriers, diluents or excipients. Such compositions may include buffers such as neutral buffered saline, sulfate buffered saline, etc.; carbohydrates such as glucose, mannose, sucrose or dextran, mannitol; proteins; polypeptides or amino acids such as glycine; antioxidants; chelating agents such as EDTA or glutathione; adjuvants (e.g., aluminum hydroxide); and preservatives. The composition of the present invention is preferably formulated for intravenous administration.

The pharmaceutical composition of the present invention may be administered in a manner suitable for the disease to be treated (or prevented). The number and frequency of administration will be determined by such factors as the patient's condition, and the type and severity of the patient's disease—although the appropriate dose may be determined by clinical trials.

When "immunologically effective amount", "anti-tumor effective amount", "tumor-suppressive effective amount" or "therapeutic amount" are indicated, the precise amount of the composition of the present invention to be administered may be determined by a physician taking into account individual differences in age, weight, tumor size, degree of infection or metastasis, and condition of the patient (subject). It may be generally noted that the pharmaceutical composition comprising T cells described herein may be administered at a dose of $10^4$ to $10^9$ cells/kg body weight, preferably at a dose of $10^5$ to $10^6$ cells/kg body weight (including all integer values in those ranges). T cell compositions may also be administered multiple times at these doses. Cells can be administered by using injection techniques well known in immunotherapy (see e.g., Rosenberg et al., NewEng.J. of Med. 319:1676, 1988). The optimal dosage and treatment regimen for a specific patient can be easily determined by a skilled person in the medical field by monitoring the patient's signs of disease and thus adjusting the treatment.

The administration of the subject composition can be carried out in any convenient manner, including by spraying, injection, swallowing, infusion, implantation or transplantation. The compositions described herein may be administered to a patient subcutaneously, intradermally, intratumoral, intratumoral, intraspinal, intramuscular, by intravenous (i.v.) injection, or intraperitoneally. In one embodiment, the T cell composition of the present invention is administered to a patient by intradermal or subcutaneous injection. In another embodiment, the T cell composition of the present invention is preferably administered by i.v. injection. The composition of T cells can be injected directly into tumors, lymph nodes or infected sites.

In certain embodiments of the present invention, cells activated and expanded using the methods described herein or other methods known in the art to expand T cells to therapeutic levels are administered to the patient in combination with any number of relevant treatment forms (e.g., before, simultaneously, or after), including but not limited to treatment with the following agents: the agents such as antiviral therapy, cidofovir and interleukin-2, cytarabine (also known as ARA-C) or natalizumab therapy in MS patients or efalizumab therapy in psoriasis patients or other therapy in PML patients. In further embodiments, the T cells of the present invention may be used in combination with chemotherapy, radiation, and immunosuppressive agents such as cyclosporin, azathioprine, methotrexate, mycophenolate and FK506, antibodies or other immunotherapeutic agents. In a further embodiment, the cell composition of the present invention is administered to a patient in combination with bone marrow transplantation, using a chemotherapeutic agent such as fludarabine, external beam radiotherapy (XRT), cyclophosphamide (e.g., before, simultaneously, or after). For example, in one embodiment, a subject may undergo a standard treatment of high-dose chemotherapy followed by peripheral blood stem cell transplantation. In some embodiments, after transplantation, the subject receives an infusion of the expanded immune cells of the present invention. In an additional embodiment, the expanded cells are administered before or after surgery.

The dose of the above treatments administered to the patient will vary with the precise attributes of the treated disorder and the recipient of the treatment. The proportion of doses administered to humans may be implemented according to practices accepted in the field. Typically, from $1\times10^6$ to $1\times10^{10}$ modified T cells of the present invention (e.g., CAR-T20 cells) may be administered to the patient by, for example, intravenous reinfusion per treatment or per course of treatment.

The Main Advantages of the Present Invention Include:

(a) The screened humanized antibodies have similar affinity.

(b) The CAR-T cells constructed by the screened humanized antibody scFv sequences have higher killing ability than CAR-T constructed by FMC63.

(c) The bispecific CAR-T cells constructed by the screened humanized antibody scFv sequences have higher killing ability against CD19 target cells than the bispecific CAR-T constructed by FMC63.

The present invention is further explained below in conjunction with specific examples. It should be understood that these examples are only for illustrating the present invention and not intend to limit the scope of the present invention. The conditions of the experimental methods not specifically indicated in the following examples are usually in accordance with conventional conditions, e.g. the conditions described in Sambrook et al., Molecular Cloning: A Laboratory Manual (New York: Cold Spring Harbor Laboratory Press, 1989), or according to the conditions recommended by the manufacturer. Unless otherwise stated, percentages and parts are percentages by weight and parts by weight.

Example 1 Design of Humanized Antibodies

FMC63 chimeric antibody against human CD19 antigen was used as maternal antibody. Based on the amino acid sequences of its heavy chain and light chain variable regions, the skeleton regions were replaced by humanization, and the humanized antibody against human CD19 antigen was designed.

Through software, 7 humanized light chain variable regions (VL1-VL7, the amino acid sequences are as shown in SEQ ID NOs: 1-7) and 10 humanized heavy chain variable regions (VH1-VH10, the amino acid sequences are as shown in SEQ ID NOs: 8-17) were designed and obtained. A number of humanized antibody sequences containing different heavy chain variable regions and light chain variable regions can be obtained by the combination of the light chain variable regions and the heavy chain variable regions described above. In subsequent examples, the affinity of the humanized antibodies is further detected.

Example 2 the Affinity Activity of Different Antibodies Determined by Biacore

Part of the antibodies in Example 1 were tested for affinity, and the composition of the heavy chain variable regions and the light chain variable regions of the antibodies to be tested are shown in Table 1.

HEK293 cells were used to express the antibodies to be tested and Protein A was used for purification. The surface plasmon resonance technique (SPR) was used for determination, and the Fc capture method was used for antibody fixation.

TABLE 1

Affinity Test Results of Humanized Antibodies

| Antibody No. | Antibody structure | $K_d$(1/s) | KD (M) |
|---|---|---|---|
| FMC63 | FMC63 | 1.29E−04 | 4.28E−09 |
| 6 | VH2 + VL3 | 3.95E−04 | 4.47E−08 |
| 12 | VH4 + VL3 | 4.37E−04 | 5.61E−08 |
| 5 | VH2 + VL2 | 5.26E−04 | 6.68E−08 |
| 4 | VH2 + VL1 | 5.68E−04 | 6.98E−08 |
| 10 | VH4 + VL1 | 5.84E−04 | 8.10E−08 |
| 11 | VH4 + VL2 | 6.05E−04 | 8.92E−08 |
| 13 | VH5 + VL1 | 6.37E−04 | 9.97E−08 |
| 8 | VH3 + VL2 | 6.38E−04 | 1.09E−07 |
| 7 | VH3 + VL1 | 6.88E−04 | 1.11E−07 |
| 15 | VH5 + VL3 | 1.43E−03 | 1.42E−08 |
| 9 | VH3 + VL3 | 1.59E−03 | 1.58E−08 |
| 14 | VH5 + VL2 | 1.80E−03 | 1.48E−08 |
| 16 | VH6 + VL4 | 4.93E−03 | 2.10E−05 |
| 17 | Negative control | 7.15E−03 | 3.39E−07 |
| 2 | VH1 + VL2 | 7.38E−03 | 7.95E−09 |
| 1 | VH1 + VL1 | 8.08E−03 | 5.76E−08 |
| 3 | VH1 + VL3 | 7.94E−02 | 4.07E−08 |

The results show that the affinity of VH2+VL3, VH4+VL3, and VH2+VL2 in the humanized antibodies to be tested was relatively higher. In the table, FMC63 is a chimeric antibody with a human Fc fragment, and the negative control is the control without the capture antibody for affinity test.

Example 3 Preparation and Expression of CAR-T Cells

Mononuclear cells were isolated from donor blood, density gradient centrifugation was performed using Histopaque-1077 (Sigma-Aldrich), and T cells were enriched (EasySep human T cell enrichment kit, Stemcell Technologies). Anti-CD3/anti-CD28 magnetic beads were used to activate, culture and expand T cells. The culture medium was X-vivo15 (300 IU/ml rhIL2), and all cells were cultured in a constant temperature incubator at 37° C., 5% $CO_2$.

The CD19-targeted CAR-T cells were constructed using part of the antibodies designed in Example 1. The lentivirus was packaged and the expression of CAR on the surface of the CAR-T was measured by flow cytometry after transfection of T cells.

The results are shown in FIG. 1. CAR expression can be detected on the surface of CAR-T cells constructed with each antibody to be tested.

Example 4 Killing Assay of CAR-T Cells

The killing ability of CAR-T cells constructed in Example 3 was tested by real-time cell assay (RTCA) using HeLa cells stably expressing CD19.

HeLa-CD19 target cells were cultured overnight, and then the effector cells (FMC63 CAR-T cells, humanized CD19 CAR-T cells prepared in Example 3, untransfected T cells): HeLa-CD19 target cells were mixed and cultured at a number ratio of 1:1, and the killing of the effector cells to the target cells was detected by RTAC.

Figure 2:
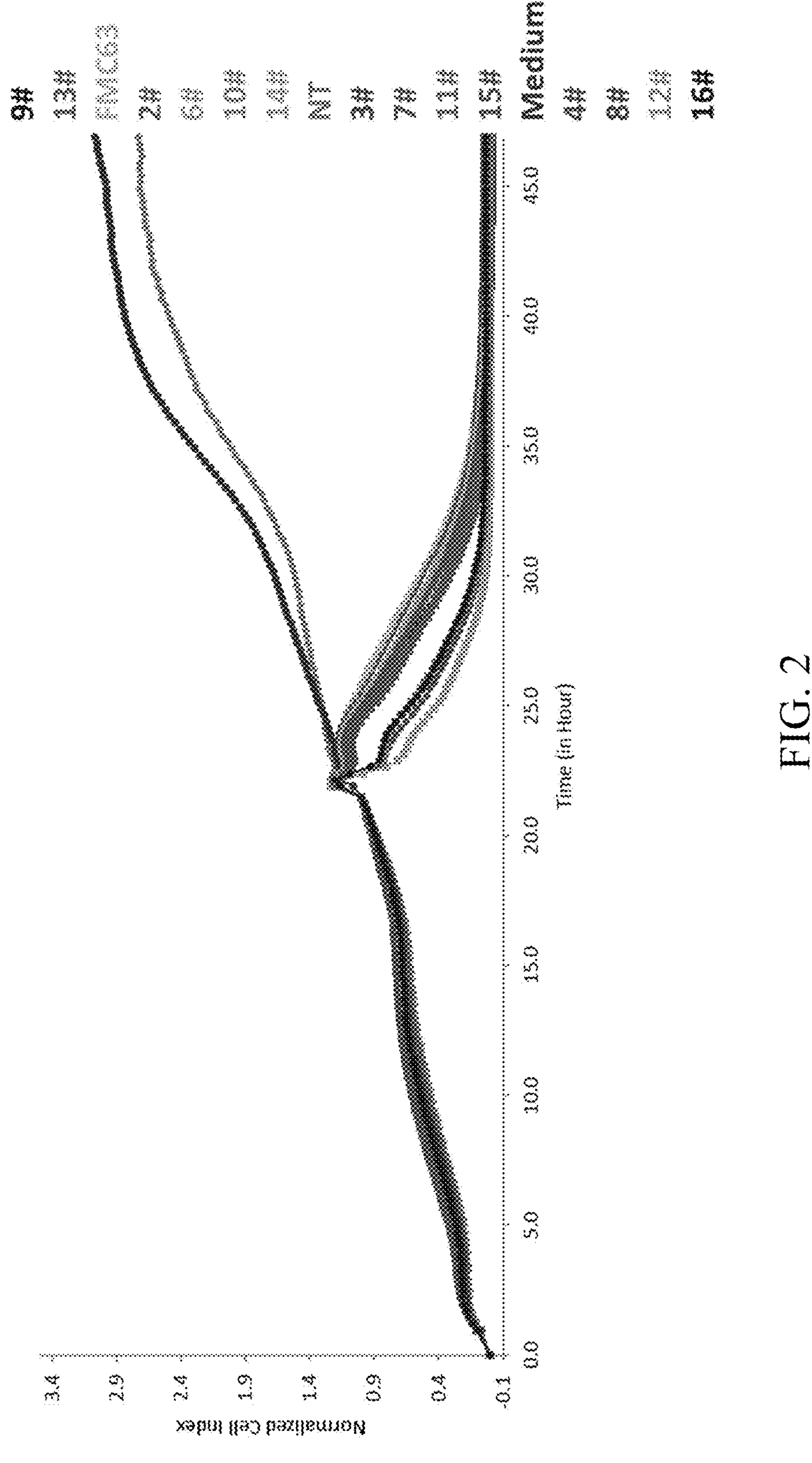
FIG. 2 shows the killing of CAR-T cells modified with FMC63 and humanized FMC63 antibody scFv on Hela-CD19 cells (RTCA assay). Each number in the figure represents the CAR-T cell constructed with the corresponding numbered antibody, and its corresponding antibody structure is shown in Table 1.

The results are shown in FIG. 2. NT control group (untransfected T cells control group) and culture medium control group (blank control group) do not kill Hela-CD19 cells, while CAR-T cells constructed by humanized scFv show significant killing ability to target cells. Compared with the killing ability of CAR-T cells constructed by FMC63 (FMC63 CAR-T), 11 #(L3H1), 1 #(L1H1), 6 #(L2H1), 16 #(L4H6) have significantly improved killing ability to CD19.

Example 5 Luciferase Detection of CAR-T Cells Killing Target Cell Nalm6

The killing ability was detected using tumor target cells labeled with luciferase. By transferring luciferase gene into target cells, Nalm6-Luc of stable cell lines were obtained after cloning and screening. During the experiment, luciferin substrate is added, and luciferase can react with luciferin to produce fluorescence. The activity of luciferase can be determined by detecting the intensity of fluorescence, and the survival ratio of cells can be detected to obtain the killing effect of each CAR-T cell.

Figure 3:
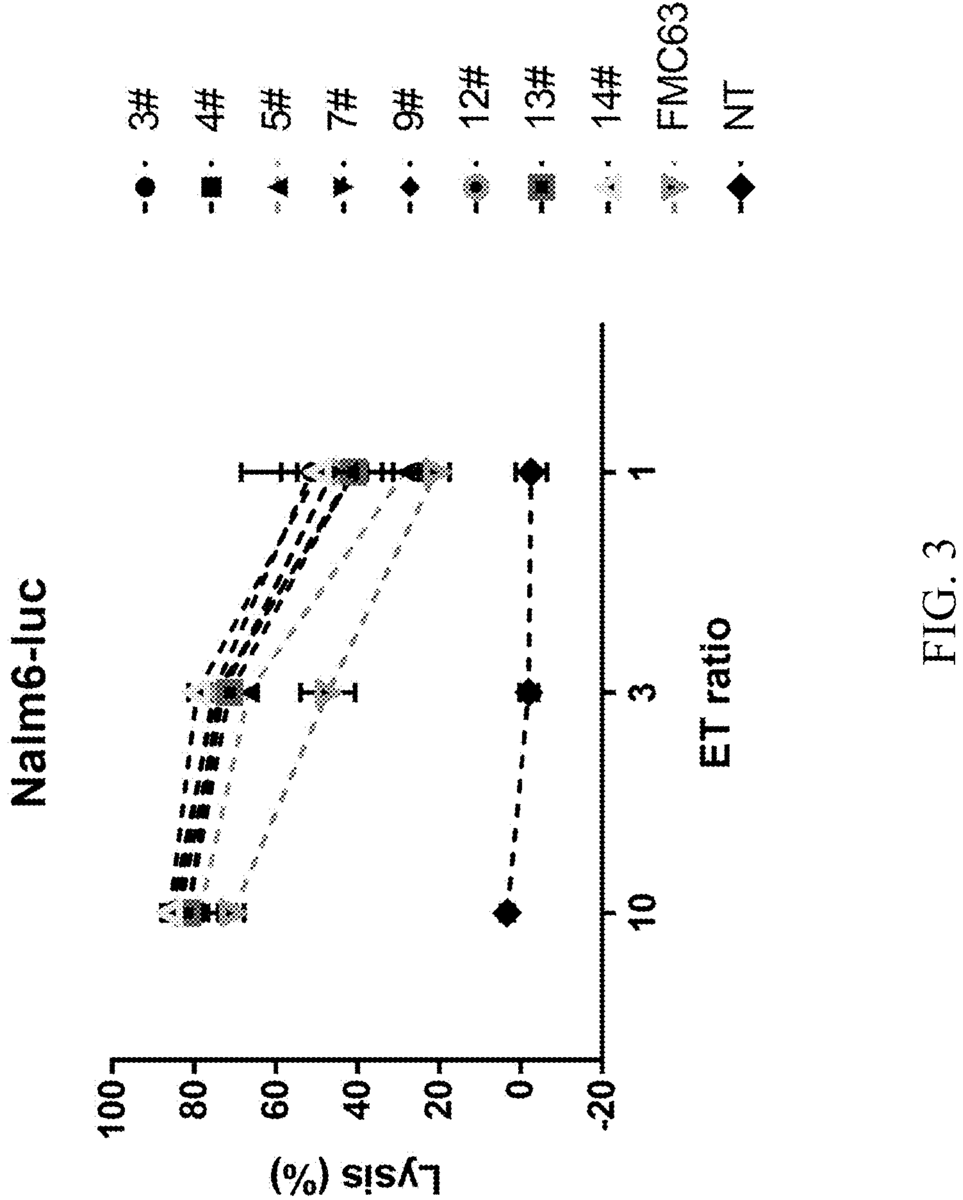
FIG. 3 shows a comparison of the killing ability of CAR-T cells modified with FMC63 and humanized FMC63 antibody scFv on Nalm6-luc cells under different effect-target ratios (Luciferase assay). Each number in the figure represents the CAR-T cell constructed with the corresponding numbered antibody, and its corresponding antibody structure is shown in Table 1.

The results are shown in FIG. 3. CAR-T cells constructed by humanized scFv show significantly higher killing ability to target cells than FMC63-CAR-T cells.

Example 6 the Affinity Activity of Different Antibodies Determined by Biacore

Part of the antibodies in Example 1 were tested for affinity, and the composition of the heavy chain variable regions and the light chain variable regions of the antibodies to be tested are shown in Table 2.

HEK293 cells were used to express the antibodies to be tested and Protein A was used for purification. The surface plasmon resonance technique (SPR) was used for determination, and the Fc capture method was used for antibody fixation.

TABLE 2

Affinity Test Results of Humanized Antibodies and Chimeric Antibodies

| Ligand | ka (1/Ms) | kd (1/s) | KD (M) | Rmax (RU) |
|---|---|---|---|---|
| FMC63 | 1.83E+05 | 2.38E−04 | 1.30E−09 | 80.2 |
| VH7 + VL6 | 1.30E+05 | 5.92E−04 | 4.57E−09 | 93.1 |
| VH8 + VL6 | 1.17E+05 | 3.83E−04 | 3.26E−09 | 78.3 |
| VH8 + VL5 | 1.55E+05 | 6.02E−04 | 3.87E−09 | 91.2 |
| VH9 + VL5 | 1.09E+05 | 1.86E−04 | 1.70E−09 | 81 |
| VH10 + VL5 | 1.18E+05 | 1.82E−04 | 1.55E−09 | 87 |
| VH4 + VL6 | 1.29E+05 | 1.21E−03 | 9.31E−09 | 106.8 |
| VH2 + VL6 | 1.79E+05 | 1.24E−03 | 6.93E−09 | 96.9 |
| VH2 + VL7 | 1.81E+05 | 1.16E−03 | 6.39E−09 | 96.4 |

The results show that compared with the chimeric antibody, the affinity of the antibodies to be tested decreases slightly, and the affinity of the humanized antibodies to be tested (VH9+VL5, VH10+VL5, VH8+VL6) was relatively higher, which has no significant difference with the chimeric antibody FMC63.

Example 7 Detection of Antibody Binding to Target Cells

Part of the antibodies in Example 1 were detected for surface binding to CD19-positive target cells SU-DHL-10 and Raji.

CD19-positive SU-DHL-10 or Raji cell lines were used, and humanized antibodies at different concentrations were used to bind the target cells. After binding, secondary antibodies (fluorescent labeled anti-Fc antibodies) were used for staining. After cleaning the residual antibodies, the positive rate was analyzed by flow cytometry to draw the binding curve of antibodies binding to cell surface antigens.

Figure 4:
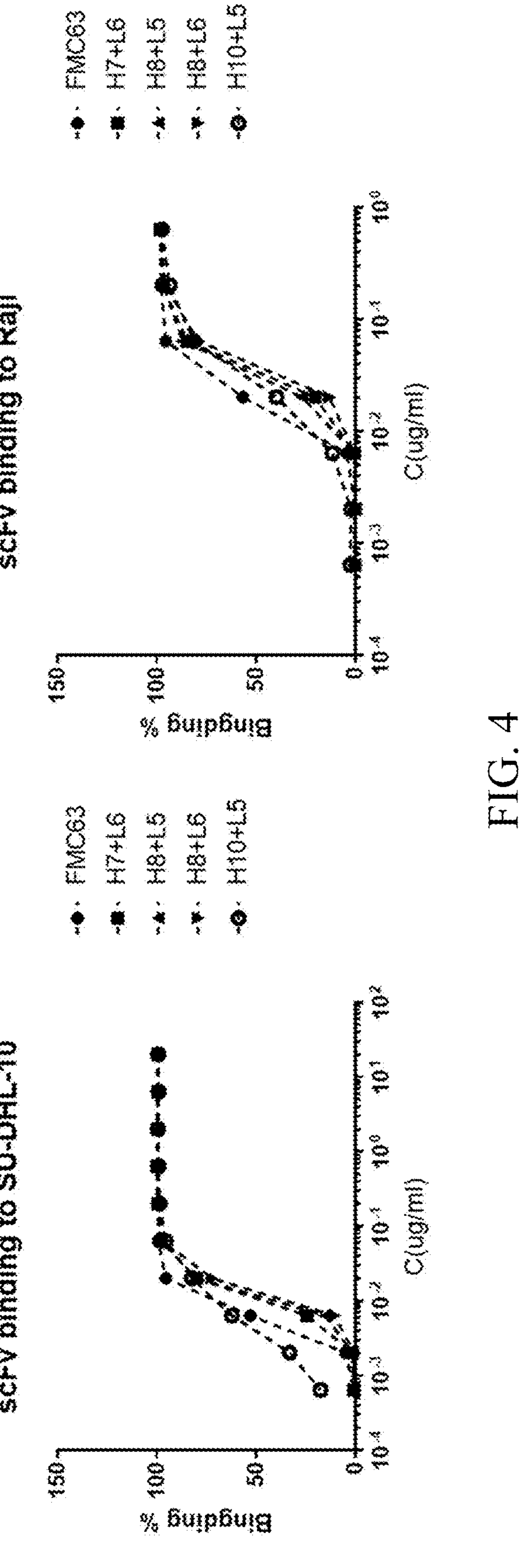
FIG. 4 shows the binding ability of FMC63 and humanized FMC63 antibodies to CD19-positive cells SU-DHL-10 and Raji cells (FACS assay). Wherein, FMC63 represents the chimeric antibody of FMC63.

The results are shown in FIG. 4. Each antibody to be tested can bind to CD19 positive target cells, and the binding ability is not significantly different from FMC63.

Example 8 Preparation and Expression of CAR-T Cells

Humanized CAR-T cells were constructed using a similar approach to Example 3 using part of the antibodies designed in Example 1.

Different detection methods (protein L, anti-FMC63 antibody, CD19 antigen) were used to detect the expression of CAR, and the expression rates were compared.

Figure 5:
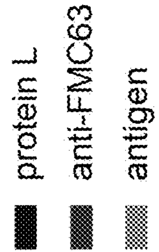
FIG. 5 shows the positive rate of CAR molecules on the surface of CAR-T cells modified with FMC63 and humanized FMC63 antibody scFv tested with different flow assay reagents.
Figure 5:
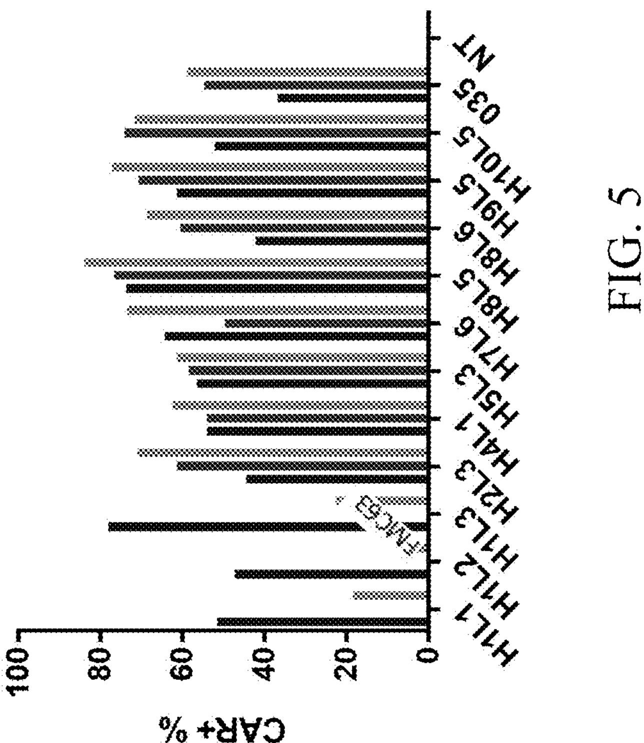

The results are shown in FIG. 5. Different degrees of CAR expression can be detected on the surface of CAR-T cells constructed with each antibody to be tested.

Example 10 Detection of CAR-T Cell Killing by RTCA

The method similar to Example 4 was used to detect the killing of target cell Hela-CD19 by CAR-T cells constructed in Example 8 through real-time cell assay (RTCA).

Figure 6:
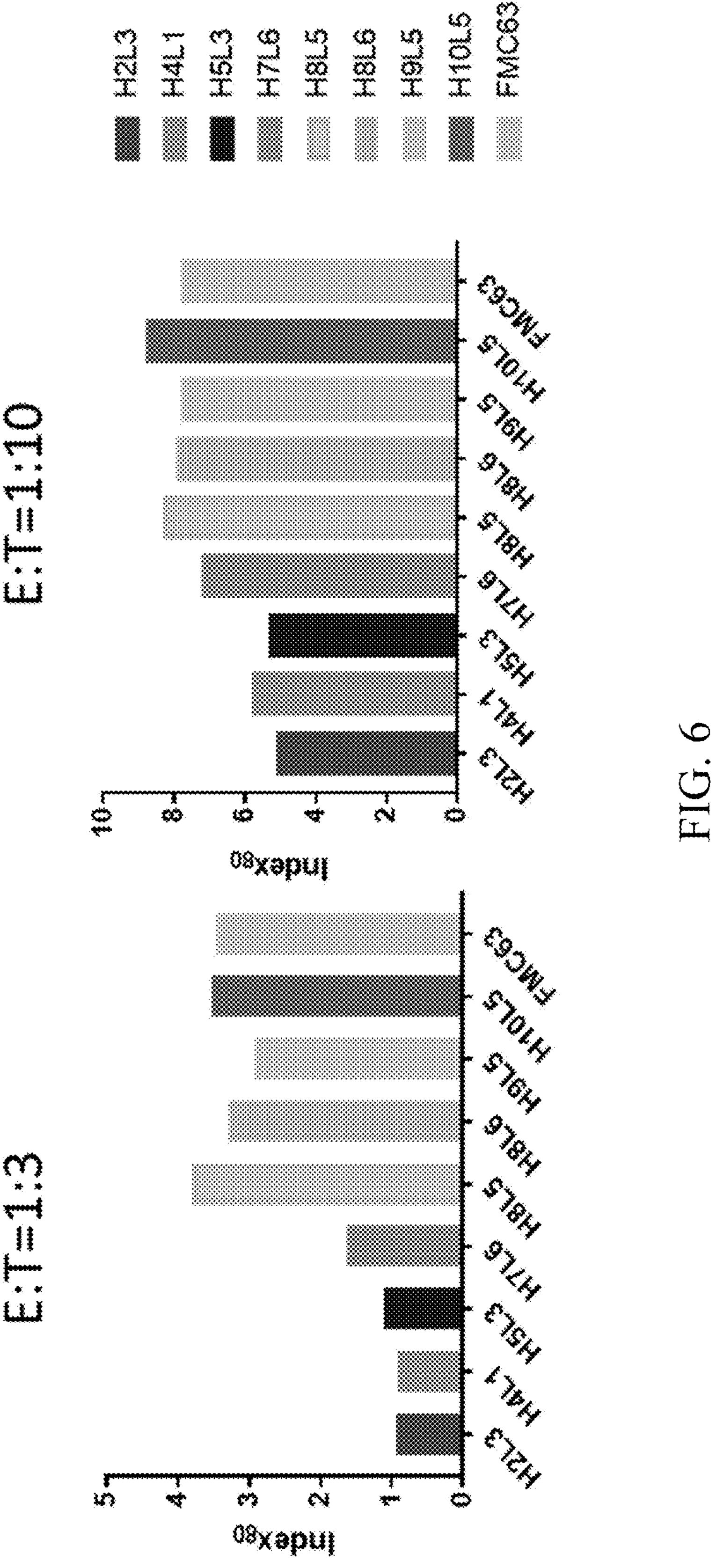
FIG. 6 shows the killing ability of CAR-T cells modified with FMC63 and humanized FMC63 antibody scFv on Hela-CD19 target cells under different effect-target ratios (RTCA assay, Index80 represents the number of hours required for 80% target cells to be killed).

The results are shown in FIG. 6. CAR-T cells constructed by humanized scFv show significant killing ability to target cells, and some humanized CAR-T cells have better killing ability than FMC63 CAR-T cells.

Example 11 Detection of CAR-T Cell Killing by Luciferase Assay

The method similar to Example 5 was used to detect the killing of the target cells Nalm6 and Raji by the CAR-T cells constructed in Example 8.

Figure 7:
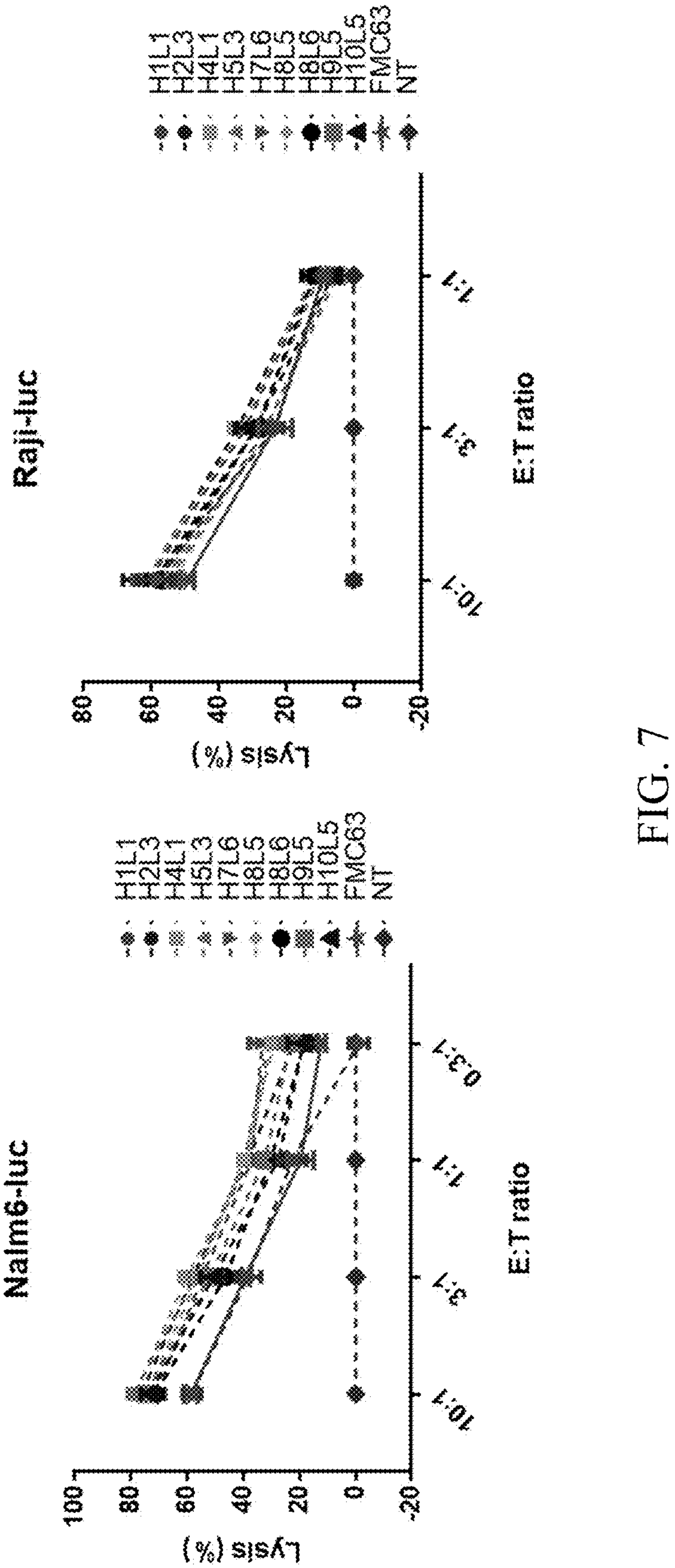
FIG. 7 shows a comparison of the killing ability of CAR-T cells modified with FMC63 and humanized FMC63 antibody scFv on Nalm6-luc and Raji-luc target cells under different effect-target ratios.

The results are shown in FIG. 7. CAR-T cells constructed by humanized scFv show significantly higher killing ability to target cells than FMC63-CAR-T cells.

Example 12 the Release of IFNγ in the Process of CAR-T Cells Killing Target Cells Nalm6 and Raji After the end of the target cell killing experiment in Example 8, the final supernatant was taken and the cytokine IFNγ therein was determined using ELISA.

Figure 8:
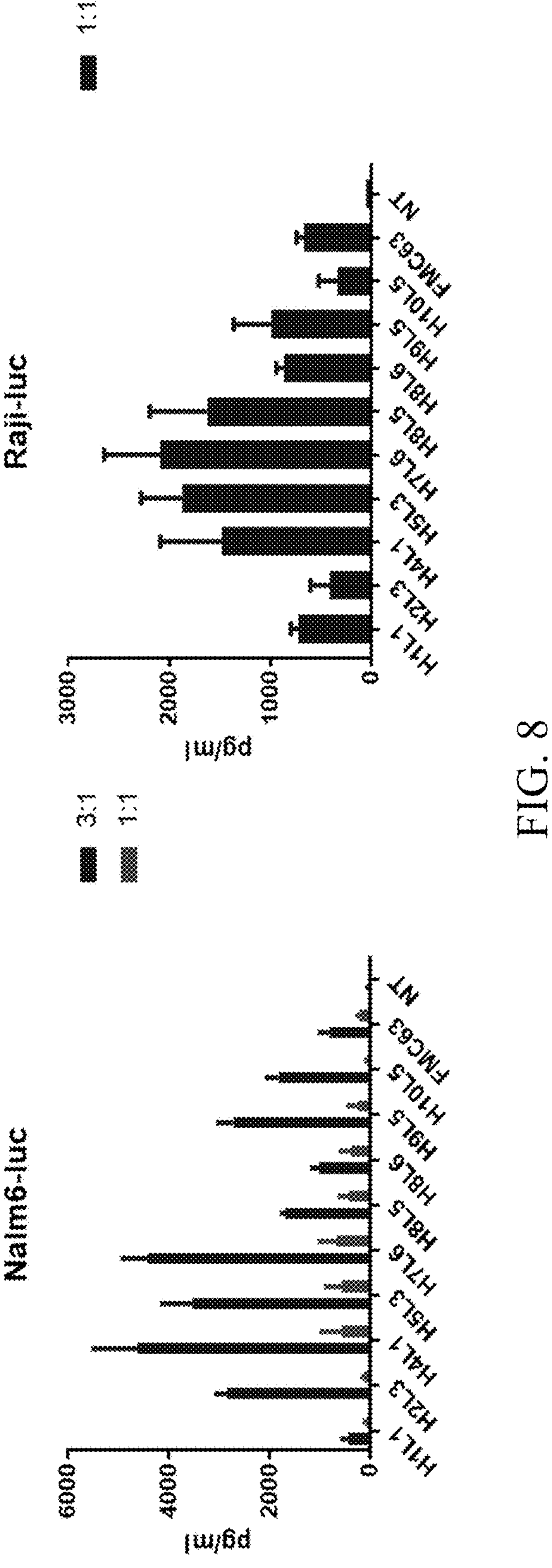
FIG. 8 shows the release of IFNγ by CAR-T cells modified with FMC63 and humanized FMC63 antibody scFv during the process of killing Nalm6-luc and Raji-luc target cells under different effect-target ratios.

The results are shown in FIG. 8. Some CAR-T cells constructed by humanized scFv produce high levels of INF-γ release to target cells Nalm6 and Raji.

Example 13 Detection of In Vivo Killing Activity

NOG mice aged 6-12 weeks were selected and $3\times10^5$ Raji cells were injected subcutaneously. After 6 days, the burden of tumor grafts was detected and the mice were divided into groups with equivalent tumor burden. The CAR-T cells constructed in Example 8 were respectively injected one day after grouping, and the tumor volume burden of mice was evaluated after CAR-T treatment. Each mouse was injected intraperitoneally with 3 mg of d-luciferin (Perkin Elmer Life Sciences) and photographed with Xenogen IVIS Imaging System (Perkin Elmer Life Sciences) four minutes later for 30 s exposure. The bioluminescence signal is calculated according to the amount of photons emitted. The amount of photons is normalized using exposure time and surface area. Finally, the amount of photons/s/$cm^2$/steradian (p/s/$cm^2$/sr) is obtained.

Figure 9:
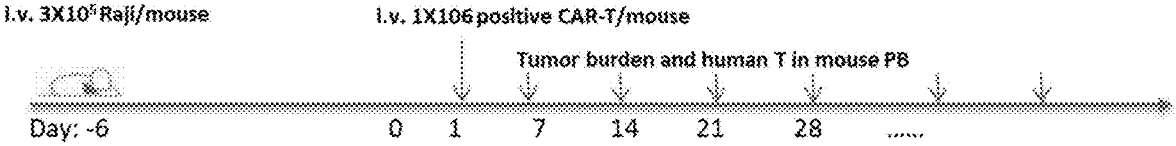
FIG. 9 shows a comparison of the efficacy of CAR-T cells modified with FMC63 and humanized FMC63 antibody scFv against Raji-modeled NOG mice in vivo.
Figure 9:
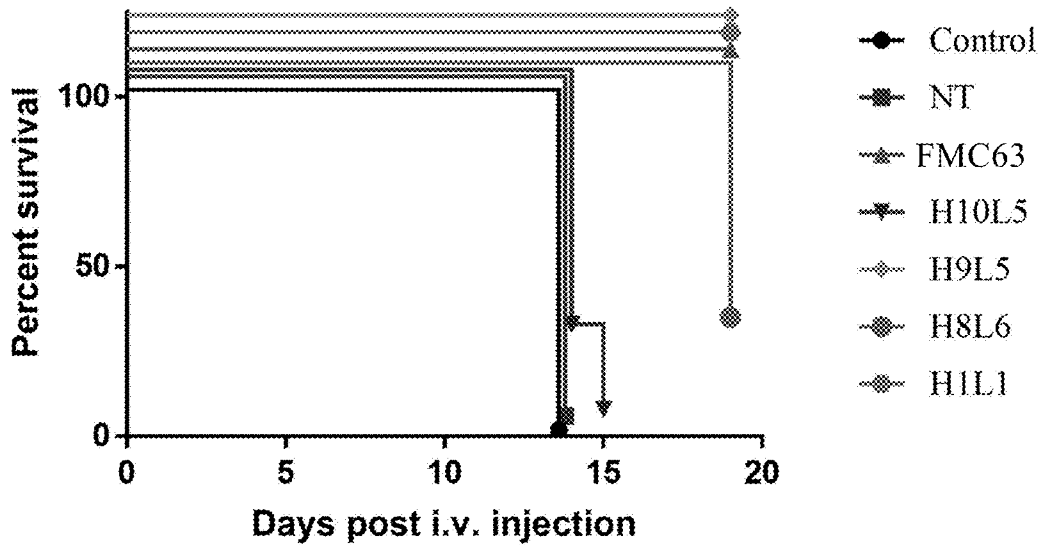
Figure 9:
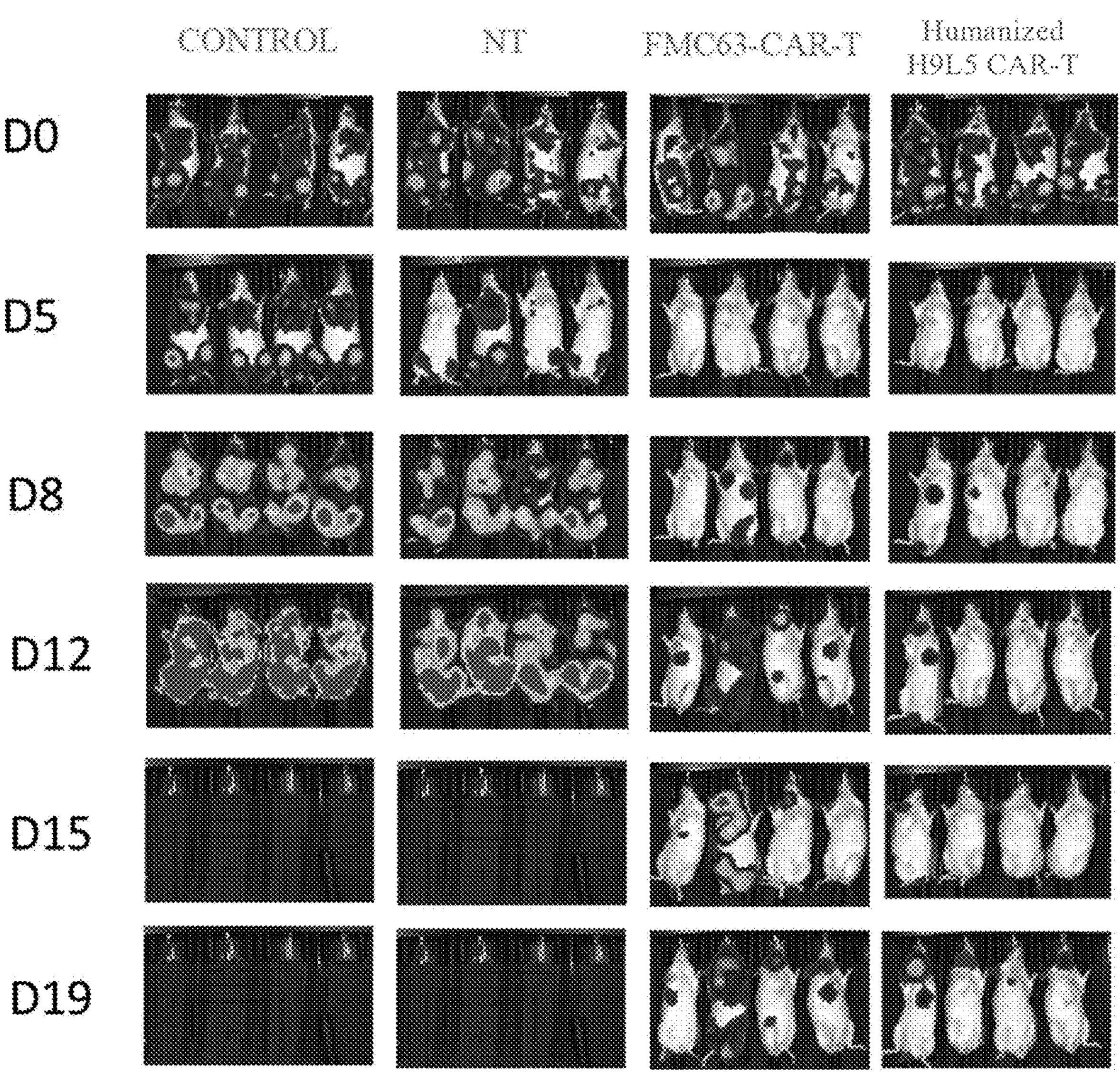

The results show that the CAR-T cells modified with humanized CD19 antibodies VH9+VL5, VH10+VL5 and VH8+VL6 can eliminate the tumor of mice modeled with Raji cells subcutaneously and prolong the survival time of the mice. Among them, the humanized CD19 antibody VH9+VL5 modified CAR-T cells have the best effect, as shown in FIG. 9, which can more effectively eliminate the tumor of Raji cell modeled mice, and which anti-tumor effect is better than that of FMC63 modified CAR-T cells.

Example 14 Non-Specific Detection of CAR-T Cells

The Lucierase method was used to detect the non-specific killing of the CAR-T cells constructed in Example 8. Raji-KO19 and Nalm6-KO19 cells knocked out of CD19, as well as K562 and CCRF cells that do not express CD19 on the cell surface were used as target cells to detect the killing of CAR-T cells on the above cells.

Figure 10:
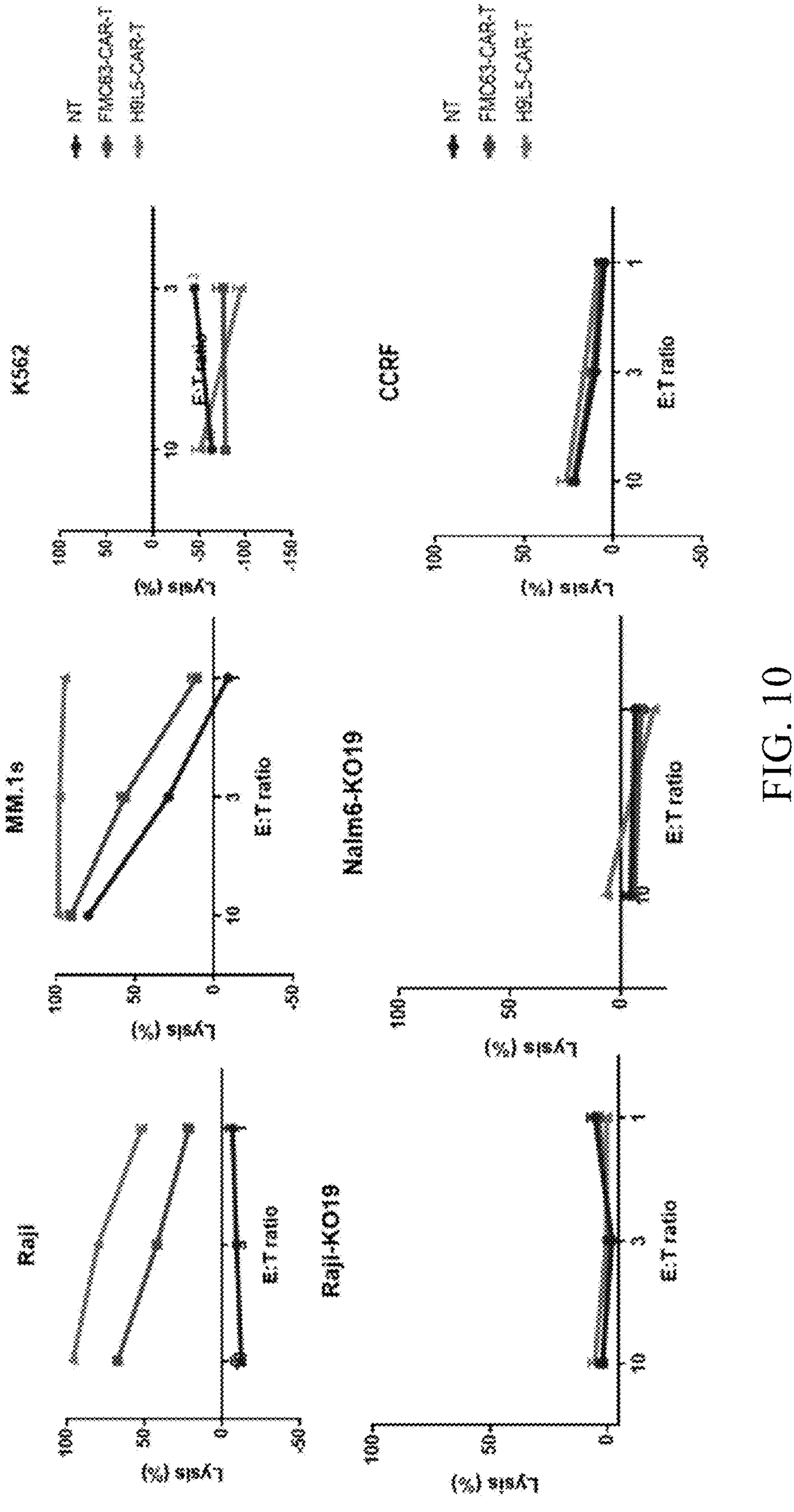
FIG. 10 shows that CAR-T cells modified with FMC63 and humanized FMC63 antibody scFv (H9L5) do not kill negative target cells (Luciferase assay).

The results are shown in FIG. 10. CAR-T cells modified with humanized CD19 antibodies do not exhibit non-specific killing and do not kill cells that do not express CD19.

Example 15 Dual CAR after Humanization in Animals

Figures 12A, 12B, 12C:
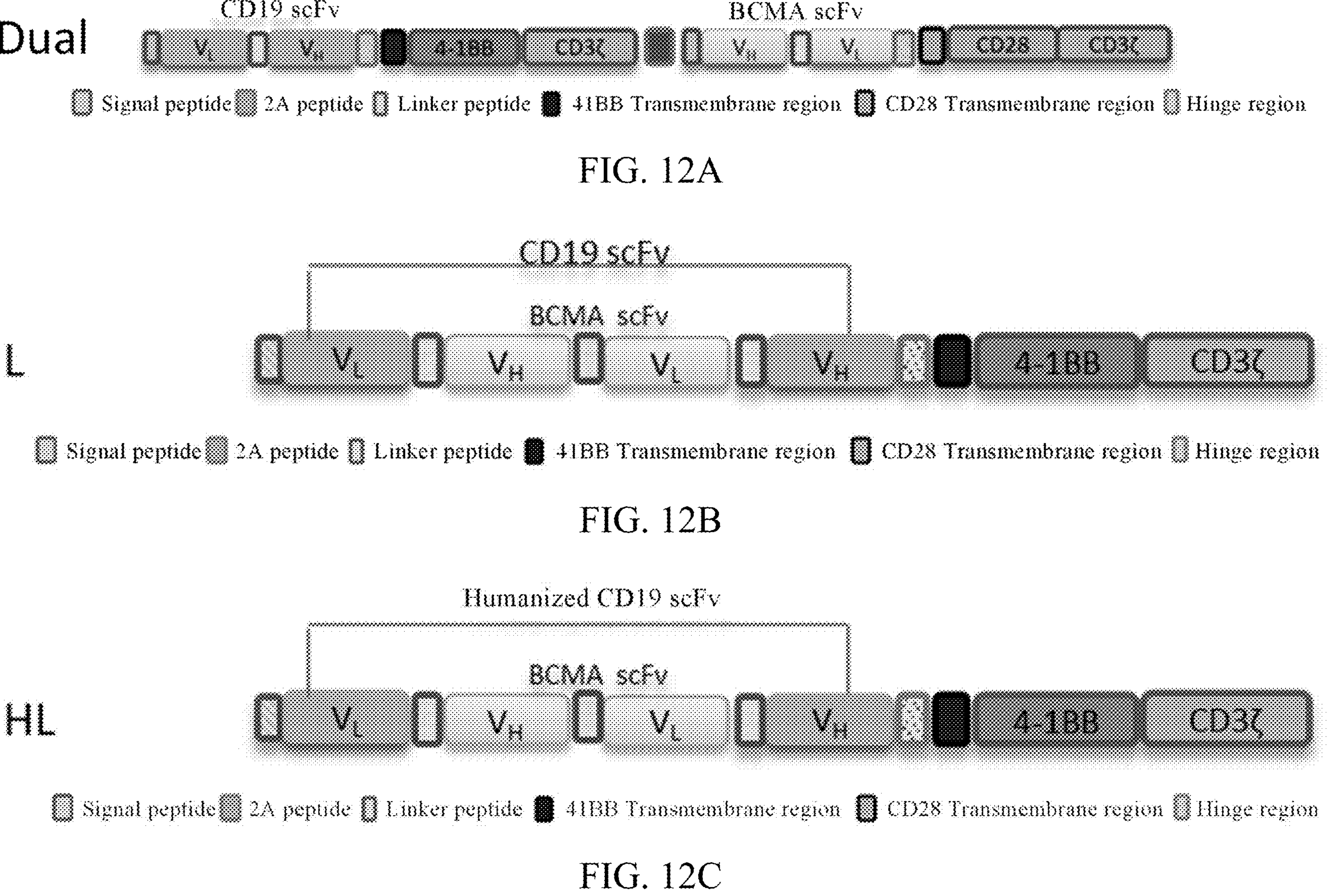
FIG. 12A shows the structure of the dual CAR constructed in Example 15.
FIG. 12B shows the structure of the mouse-derived dual CAR constructed in Example 16.
FIG. 12C shows the structure of the humanized dual CAR constructed in Example 16.

The humanized scFv and FMC63 and BCMA antibody were used to construct dual CAR-T cells targeting both BCMA and CD19 respectively, and the killing activity in vivo was detected. The structure of the dual CAR is shown in FIG. 12A. The heavy chain variable region of BCMA scFv is shown in SEQ ID NO: 21, and the light chain variable region is shown in SEQ ID NO: 20.

NOG mice aged 6-12 weeks were selected and $3\times10^5$ Raji cells were injected subcutaneously. After 6 days, the burden of tumor grafts was detected and the mice were divided into groups with equivalent tumor burden. The CAR-T cells constructed above were injected one day after grouping, and the tumor volume burden of mice was evaluated after CAR-T treatment. Each mouse was injected intraperitoneally with 3 mg of d-luciferin (Perkin Elmer Life Sciences) and photographed with Xenogen IVIS Imaging System (Perkin Elmer Life Sciences) four minutes later for 30 s exposure. The bioluminescence signal is calculated according to the amount of photons emitted. The amount of photons is normalized using exposure time and surface area. Finally, the amount of photons/s/cm$^2$/steradian (p/s/cm$^2$/sr) is obtained.

Figure 11:
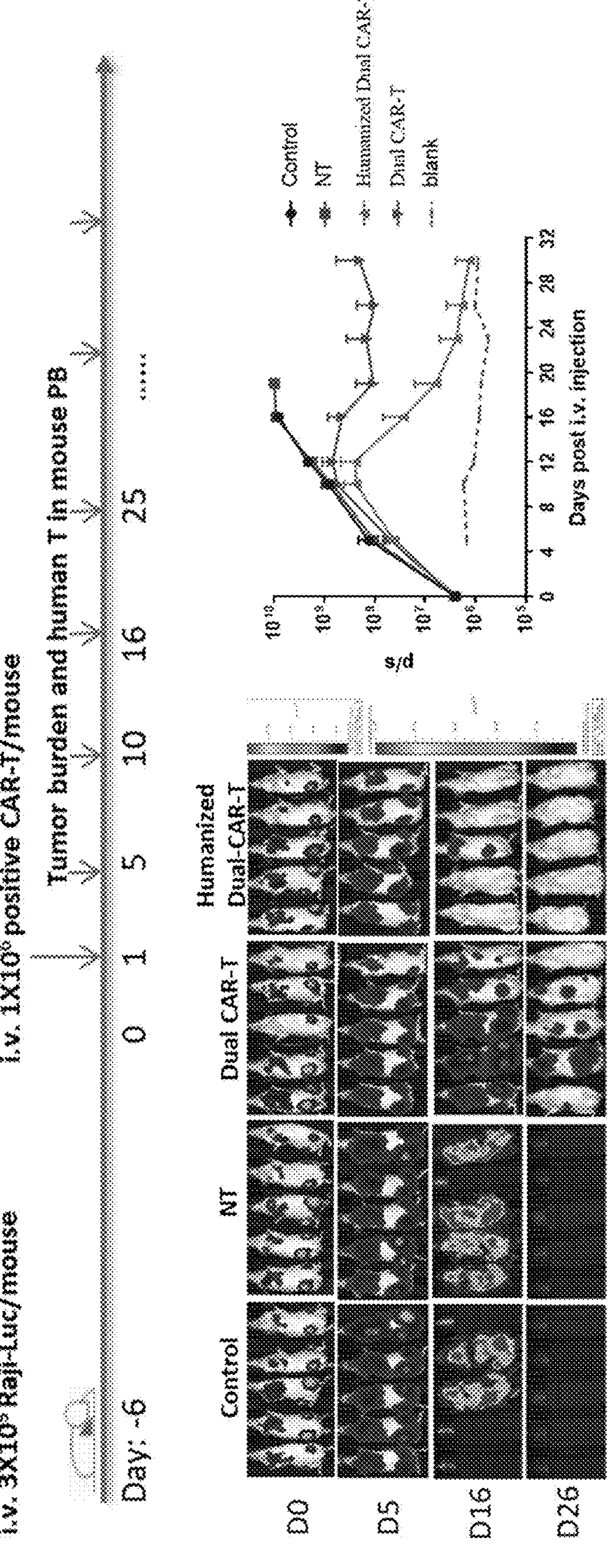
FIG. 11 shows a comparison of the ability of bispecific CAR-T cells modified with FMC63 and humanized FMC63 antibody scFv (H9L5) to eliminate tumors in Raji-modeled NOG mice.

The results show that the bispecific CAR-T cells modified with humanized CD19 antibodies VH9+VL5, VH10+VL5 and VH8+VL6 all have a stronger ability to eliminate the tumor of Raji cell model mice than the bispecific CAR-T (Dual CAR-T) modified with FMC63, and the anti-tumor effects are basically equivalent. Among them, the humanized CD19 antibody VH9+VL5 modified bispecific CAR-T cells have the best effect, as shown in FIG. 11, indicating its significant anti-tumor efficacy.

Example 16 Comparison of Killing Ability of Humanized Dual CAR-T and Mouse Dual CAR-T Humanized CD19 scFv (VH9+VL5) and FMC63 and BCMA antibodies were used to construct bispecific CAR-T cells targeting both BCMA and CD19, respectively. The structures of the bispecific CAR are shown in FIG. 12B and FIG. 12C. The heavy chain variable region of BCMA scFv is shown in SEQ ID NO: 21, and the light chain variable region is shown in SEQ ID NO: 20.

Using a similar method in Example 5, the killing ability of constructed bispecific CAR-T cells was detected using luciferase-labeled tumor target cells.

Figure 13:
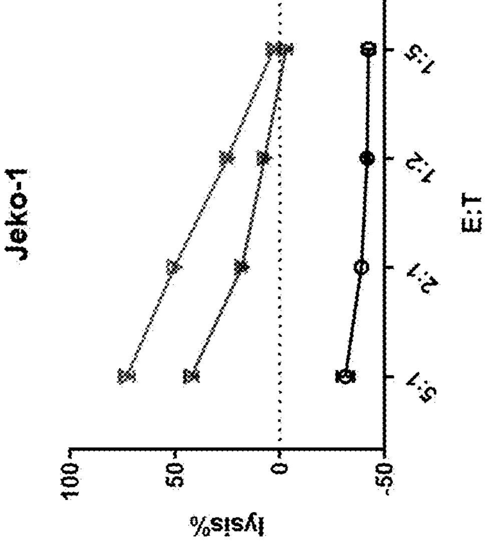
FIG. 13 shows a comparison of the killing ability of humanized dual-CAR-T and mouse-derived dual-CAR-T. Wherein, NT represents negative control, L represents mouse-derived dual CAR-T cells, and HL represents humanized dual CAR-T cells.
Figure 13:
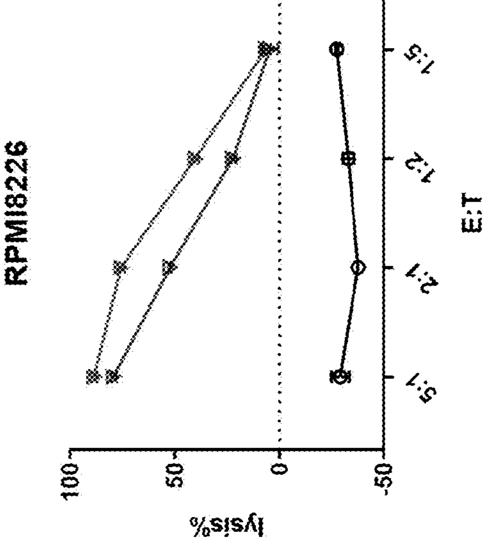
Figure 13:
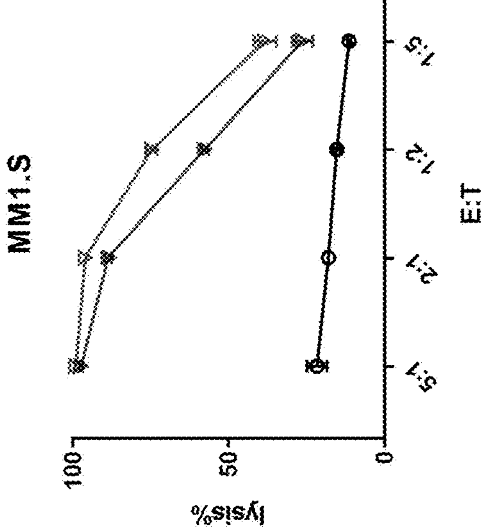
Figure 13:
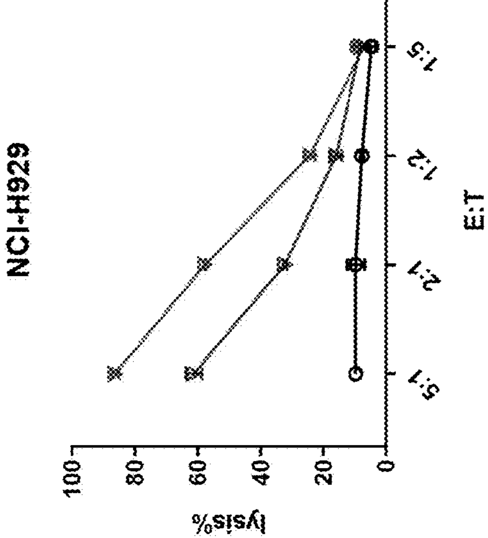
Figure 13:
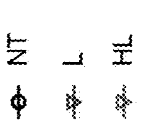
Figure 13:
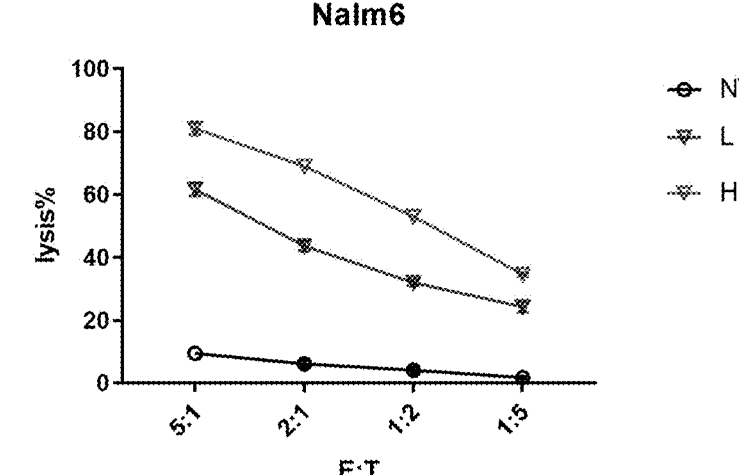

The results are shown in FIG. 13. The humanized scFv-constructed dual-CAR-T cells show significantly higher killing ability on target cells than mouse-derived dual-CAR-T cells.

Example 17 Production and Expression Test of Humanized Universal Dual CAR-T

Using the humanized dual-CAR-T cells and mouse-derived dual-CAR-T cells constructed in Example 16, and knocking out the T-cell TRAC and B2M genes, the humanized universal CAR-T cells were constructed.

Using a similar method in Example 3, different detection methods (anti-FMC63 antibody, CD19 antigen) were used to detect the expression of CAR, and the expression rate was measured, and the knockout efficiency was measured using anti-B2M and CD3 antibodies.

Figure 14:
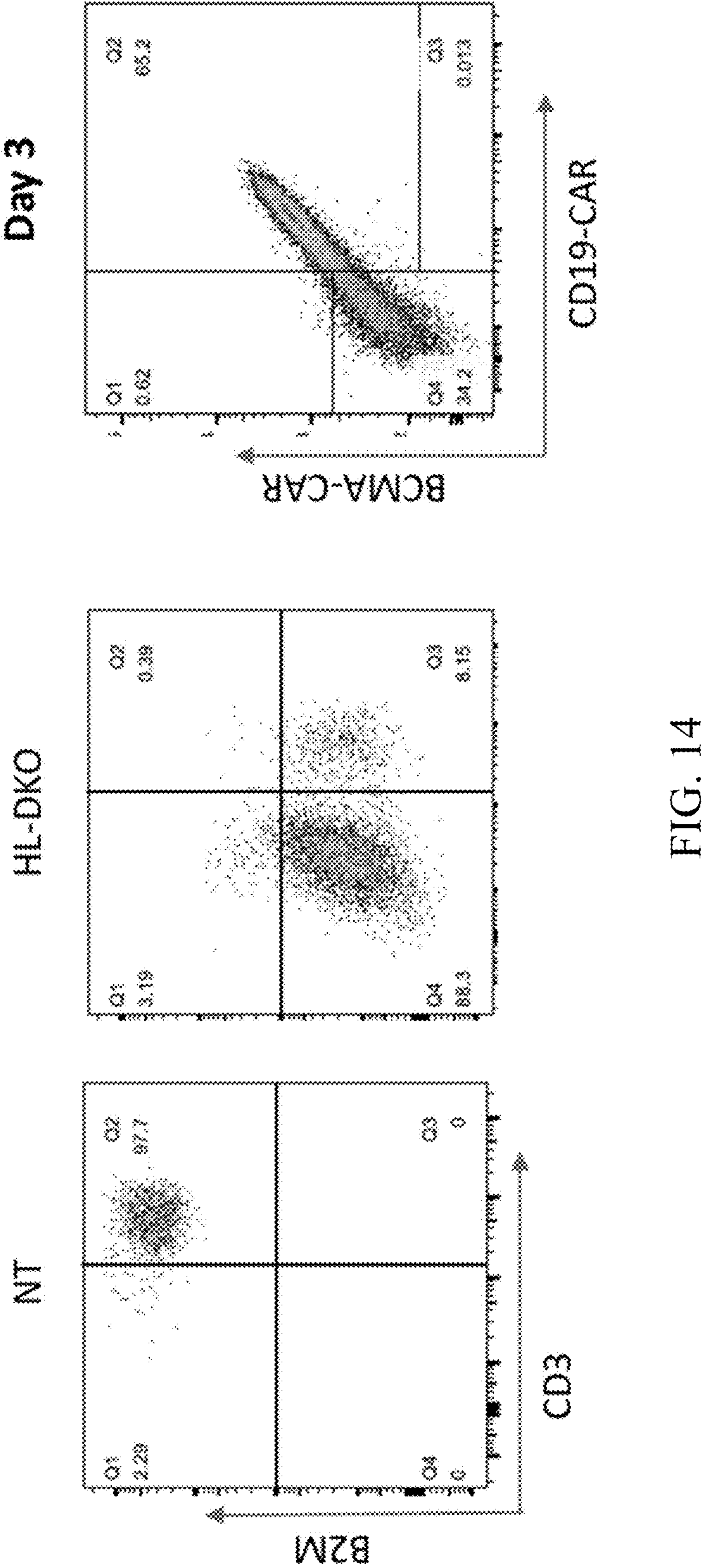
FIG. 14 shows the production of universal CAR-T of humanized dual CAR-T cells. Wherein, NT represents negative control and HL-DKO represents universal humanized dual CAR-T cells with double knockout.

The results are shown in FIG. 14. TRAC and B2M genes of universal CAR-T cells are knocked out, and CAR targeting BCMA and humanized CD19 can be expressed at the same time.

Example 18 the Killing Ability of Humanized Universal Dual CAR-T Cells and Non-Universal CAR-T Cells Using a similar method in Example 5, the killing ability of constructed dual CAR-T cells in Example 17 was detected using luciferase-labeled tumor target cells.

Figure 15:
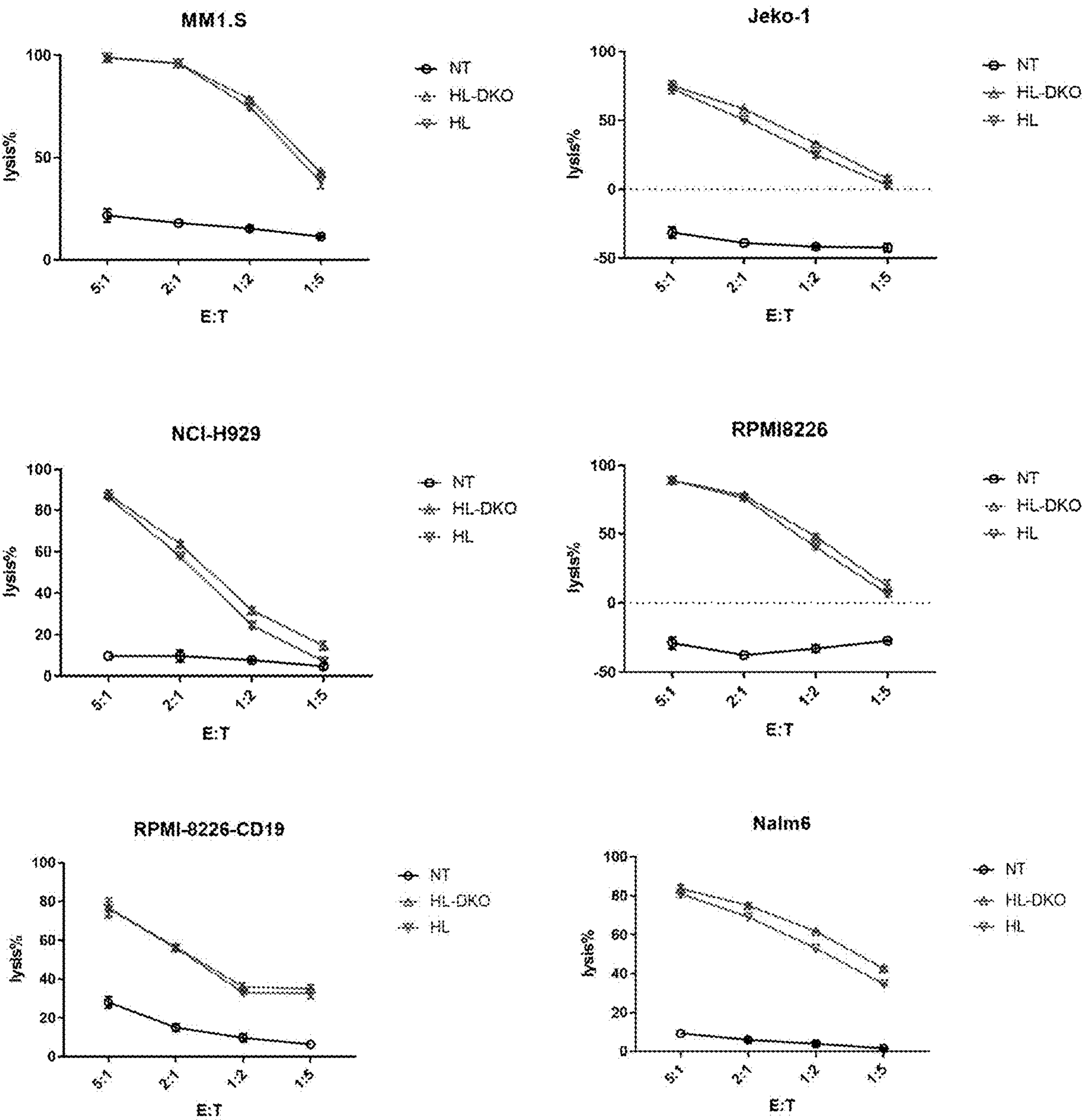
FIG. 15 shows a comparison of the killing effect of conventional CAR-T and universal CAR-T after humanization of the dual CAR-T cells. Wherein, NT represents negative control, HL-DKO represents universal humanized dual CAR-T cells with double knockout, and HL represents humanized dual CAR-T cells.

The results are shown in FIG. 15. The universal dual CAR-T cells show similar killing ability to non-universal CAR-T cells.

All literatures mentioned in the present application are incorporated by reference herein, as though individually incorporated by reference. In addition, it should be understood that after reading the above teaching content of the present invention, various changes or modifications may be made by those skilled in the art, and these equivalents also fall within the scope as defined by the appended claims of the present application.

The invention claimed is:

1. A humanized CD19 antibody, which comprises an antibody light chain variable region shown in a sequence selected from the group consisting of SEQ ID NO: 1-7, and an antibody heavy chain variable region shown in a sequence selected from the group consisting of SEQ ID NO: 8-17.

2. The humanized CD19 antibody of claim 1, which comprises an antibody light chain variable region shown in SEQ ID NO: 5 or 6, and an antibody heavy chain variable region shown in SEQ ID NO: 15, 16, or 17.

3. The humanized CD19 antibody of claim 1, wherein the antibody comprises an antibody light chain variable region shown in SEQ ID NO: 5, and an antibody heavy chain variable region shown in SEQ ID NO: 16;

the antibody comprises an antibody light chain variable region shown in SEQ ID NO: 5, and an antibody heavy chain variable region shown in SEQ ID NO: 17; or the antibody comprises an antibody light chain variable region shown in SEQ ID NO: 6, and an antibody heavy chain variable region shown in SEQ ID NO: 15.

4. A chimeric antigen receptor (CAR) targeting CD19, wherein the antigen binding domain of the CAR is an scFv comprising the heavy chain variable region and light chain variable region of the humanized CD19 antibody of claim 1.

5. A bispecific CAR, which targets CD19 and a first target, wherein, the antigen binding domain targeting CD19 in the bispecific CAR is an scFv comprising the heavy chain variable region and the light chain variable region of the humanized CD19 antibody of claim 1; and the first target is selected from the group consisting of: CD2, CD3, CD4, CD5, CD7, CD8, CD19, CD20, CD22, CD25, CD28, CD30, CD33, CD38, CD40, CD44V6, CD47, CD52, CD56, CD57, CD58, CD79b, CD80, CD86, CD81, CD123, CD133, CD137, CD151, CD171, CD276, CLL1, B7H4, BCMA, VEGFR-2, EGFR, GPC3, PMSA, CEACAM6, c-Met, EGFRvIII, ErbB2/HER2, ErbB3, HER-2, HER3, ErbB4/HER-4, EphA2, IGF1R, GD2, O-acetyl GD2, O-acetyl GD3, GHRHR, GHR, Flt1, KDR, Flt4, Flt3, CEA, CA125, CTLA-4, GITR, BTLA, TGFBR1, TGFBR2, IL6R, gp130, Lewis, TNFR1, TNFR2, PD1, PD-L1, PD-L2, PSCA, HVEM, MAGE-A, MSLN, NY-ESO-1, PSMA, RANK, ROR1, TNFRSF4, TWEAK-R, LTPR, LIFRP, LRP5, MUC1, MUC16, TCR α, TCR β, TLR7, TLR9, PTCH1, WT-1, Robo1, Frizzled, OX40,Notch-1-4, APRIL, CS1, MAGE3, Claudin 18.2, Folate receptor α, Folate receptor β, GPC2, CD70, BAFF-R, TROP-2, and a combination thereof.

6. The bispecific CAR of claim 5, wherein the structure of the bispecific CAR is as shown in Formula III or III':

L-$V_{L3}$-scFv3-$V_{H3}$-H-TM-C-CD3ζ (III),

L-$V_{H3}$-scFv3-$V_{L3}$-H1-TM-C-CD3ζ (III'), wherein, each "-" is independently a linking peptide or a peptide bond;

L is none or a signal peptide sequence;

H is a hinge region;

TM is a transmembrane domain;

C is a costimulatory signal molecule;

CD3ζ is a cytoplasmic signaling sequence derived from CD3ζ;

scFv3 is (i) the antigen binding domain targeting CD19, VH3 is the heavy chain variable region of the anti-first target antibody, and VL3 is the light chain variable region of the anti-first target antibody; or (ii) the antigen binding domain targeting the first target, VH3 is the heavy chain variable region of the anti-CD19 antibody, and VL3 is the light chain variable region of the anti-CD19 antibody.

7. The bispecific CAR of claim 5, wherein the structure of the bispecific CAR is as shown in Formula II:

L-scFv1-I-scFv2-H-TM-C-CD3ζ (II), wherein, each "-" is independently a linking peptide or a peptide bond;

L is none or a signal peptide sequence;

I is a flexible linker;

H is a hinge region;

TM is a transmembrane domain;

C is a costimulatory signal molecule;

CD3ζ is a cytoplasmic signaling sequence derived from CD3ζ; and one of scFv1 and scFv2 is the antigen binding domain targeting the first target, and the other is the antigen binding domain targeting CD19.

8. The bispecific CAR of claim 5, which comprises a first CAR targeting the first target and a second CAR targeting CD19, wherein the first CAR and the second CAR are connected by a self-shearing element.

9. A polynucleotide encoding:

(i) the humanized CD19 antibody of claim 1, (ii) a chimeric antigen receptor (CAR) targeting CD19 wherein the antigen binding domain is an scFv comprising the heavy chain variable region and the light chain variable region of the humanized CD19 antibody of claim 1, or (iii) a bispecific CAR that targets CD19 and a first target, wherein the antigen binding domain targeting CD19 in the bispecific CAR is the humanized CD19 antibody of claim 1.

10. An engineered immune cell, wherein the immune cell has the polynucleotide of claim 9 integrated in chromosome.

11. The engineered immune cell of claim 10, wherein the engineered immune cell comprises a universal CAR-T cell.

12. The engineered immune cell of claim 11, wherein the universal CAR-T cell further comprises a knockout of the TRAC and B2M genes.

13. A formulation, which comprises the engineered immune cell of claim 10, and a pharmaceutically acceptable carrier, diluent or excipient.

14. An engineered immune cell, which (i) comprises an exogenous first expression cassette and an exogenous second expression cassette, wherein the first expression cassette is for expressing a first CAR targeting a first target, and the second expression cassette is for expressing a second CAR targeting CD19; or (ii) expresses the first CAR targeting the first target and the second CAR targeting CD19;

wherein, the antigen binding domain targeting CD19 in the second CAR is an scFv comprising the heavy chain variable region and light chain variable region of the humanized CD19 antibody of claim 1; and the first target is selected from the group consisting of: CD2, CD3, CD4, CD5, CD7, CD8, CD19, CD20, CD22, CD25, CD28, CD30, CD33, CD38, CD40, CD44V6, CD47, CD52, CD56, CD57, CD58, CD79b, CD80, CD86, CD81, CD123, CD133, CD137, CD151, CD171, CD276, CLL1, B7H4, BCMA, VEGFR-2, EGFR, GPC3, PMSA, CEACAM6, c-Met, EGFRvIII, ErbB2/HER2, ErbB3, HER-2, HER3, ErbB4/HER-4, EphA2, IGF1R, GD2, O-acetyl GD2, O-acetyl GD3, GHRHR, GHR, Flt1, KDR, Flt4, Flt3, CEA, CA125, CTLA-4, GITR, BTLA, TGFBR1, TGFBR2, IL6R, gp130, Lewis, TNFR1, TNFR2, PD1, PD-L1, PD-L2, PSCA, HVEM, MAGE-A, MSLN, NY-ESO-1, PSMA, RANK, ROR1, TNFRSF4, TWEAK-R, LTPR, LIFRP, LRP5, MUC1, MUC16, TCR α, TCR β, TLR7, TLR9, PTCH1, WT-1, Robol, Frizzled, OX40, Notch-1-4, APRIL, CS1, MAGE3, Claudin 18.2, Folate receptor α, Folate receptor β, GPC2, CD70, BAFF-R, TROP-2, and a combination thereof.

15. A formulation, which comprises the humanized CD19 antibody of claim 1, and a pharmaceutically acceptable carrier, diluent, or excipient.

16. A method of treating a disease comprising the step of administering to a subject in need of treatment a therapeutically effective amount of the formulation of claim 15, wherein the disease is cancer.

* * * * *

SEQUENCE LISTING

```
<160> NUMBER OF SEQ ID NOS: 30

<210> SEQ ID NO 1
<211> LENGTH: 107
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Humanized light chain variable region L1

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
```

```
65                  70                  75                  80

Glu Asp Ile Ala Thr Tyr Tyr Cys Gln Gln Gly Asn Thr Leu Pro Tyr
                85                  90                  95

Thr Phe Gly Gly Gly Thr Lys Leu Glu Ile Lys
            100                 105


<210> SEQ ID NO 2
<211> LENGTH: 107
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Humanized light chain variable region L2

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gly Gly Thr Lys Leu Glu Ile Lys
            100                 105


<210> SEQ ID NO 3
<211> LENGTH: 107
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Humanized light chain variable region L3

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gly Gly Thr Lys Leu Glu Ile Lys
            100                 105


<210> SEQ ID NO 4
<211> LENGTH: 107
```

```
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Humanized light chain variable region L4

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Ile Ala Thr Tyr Tyr Cys Gln Gln Ala Asn Thr Leu Pro Tyr
                85                  90                  95

Thr Phe Gly Gly Gly Thr Lys Leu Glu Ile Lys
            100                 105


<210> SEQ ID NO 5
<211> LENGTH: 107
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Humanized light chain variable region L5

<400> SEQUENCE: 5

Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Lys
            100                 105


<210> SEQ ID NO 6
<211> LENGTH: 107
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Humanized light chain variable region L6

<400> SEQUENCE: 6

Asp Ile Gln Met Thr Gln Ser Pro Ser Ser Leu Ser Ala Ser Val Gly
```

```
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Gly Ala Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Lys
            100                 105


<210> SEQ ID NO 7
<211> LENGTH: 107
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Humanized light chain variable region L7

<400> SEQUENCE: 7

Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Lys
            100                 105


<210> SEQ ID NO 8
<211> LENGTH: 120
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Humanized heavy chain variable region H1

<400> SEQUENCE: 8

Gln Val Gln Leu Gln Glu Ser Gly Pro Gly Leu Val Lys Pro Ser Gln
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Asn Ser Ala Leu Lys
    50                  55                  60
```

```
Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg His Tyr Tyr Tyr Gly Gly Ser Tyr Ala Met Asp Tyr Trp Gly Gln
            100                 105                 110

Gly Thr Thr Val Thr Val Ser Ser
        115                 120


<210> SEQ ID NO 9
<211> LENGTH: 120
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Humanized heavy chain variable region H2

<400> SEQUENCE: 9

Gln Val Gln Leu Gln Glu Ser Gly Pro Gly Leu Val Lys Pro Ser Gln
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Asn Ser Ala Leu Lys
    50                  55                  60

Ser Arg Val Thr Ile Ser Lys Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Thr Val Thr Val Ser Ser
        115                 120


<210> SEQ ID NO 10
<211> LENGTH: 120
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Humanized heavy chain variable region H3

<400> SEQUENCE: 10

Gln Val Gln Leu Gln Glu Ser Gly Pro Gly Leu Val Lys Pro Ser Gln
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Asn Ser Ala Leu Lys
    50                  55                  60

Ser Arg Leu Thr Ile Ser Lys Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95
```

```
Lys His Tyr Tyr Tyr Gly Gly Ser Tyr Ala Met Asp Tyr Trp Gly Gln
            100                 105                 110

Gly Thr Thr Val Thr Val Ser Ser
        115                 120


<210> SEQ ID NO 11
<211> LENGTH: 120
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Humanized heavy chain variable region H4

<400> SEQUENCE: 11

Gln Val Gln Leu Gln Glu Ser Gly Pro Gly Leu Val Lys Pro Ser Gln
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ser Lys Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Thr Val Thr Val Ser Ser
        115                 120


<210> SEQ ID NO 12
<211> LENGTH: 120
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Humanized heavy chain variable region H5

<400> SEQUENCE: 12

Gln Val Gln Leu Gln Glu Ser Gly Pro Gly Leu Val Lys Pro Ser Gln
1               5                   10                  15

Thr Leu Ser Val Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ser Lys Asp Thr Ser Lys Asn Gln Val Ser Leu
65                  70                  75                  80

Lys Leu Ser Ser Leu Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Thr Val Thr Val Ser Ser
```

```
        115                 120


<210> SEQ ID NO 13
<211> LENGTH: 120
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Humanized heavy chain variable region H6

<400> SEQUENCE: 13

Gln Val Gln Leu Gln Glu Ser Gly Pro Gly Leu Val Lys Pro Ser Gln
1               5                   10                  15

Thr Leu Ser Val Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Leu
        35                  40                  45

Gly Val Ile Trp Gly Ser Glu Thr Thr Tyr Tyr Asn Ala Ala Leu Lys
    50                  55                  60

Ser Arg Leu Thr Ile Ser Lys Asp Thr Ser Lys Asn Gln Val Ser Leu
65                  70                  75                  80

Lys Leu Ser Ser Leu Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Thr Val Thr Val Ser Ser
        115                 120


<210> SEQ ID NO 14
<211> LENGTH: 120
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Humanized heavy chain variable region H7

<400> SEQUENCE: 14

Gln Val Lys Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ser Lys Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser
        115                 120


<210> SEQ ID NO 15
<211> LENGTH: 120
```

```
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Humanized heavy chain variable region H8

<400> SEQUENCE: 15

Gln Val Lys Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Asn Ser Ala Leu Lys
    50                  55                  60

Ser Arg Val Thr Ile Ser Lys Asp Thr Ser Lys Ser Gln Val Phe Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser
        115                 120


<210> SEQ ID NO 16
<211> LENGTH: 120
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Humanized heavy chain variable region H9

<400> SEQUENCE: 16

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser
        115                 120


<210> SEQ ID NO 17
<211> LENGTH: 120
<212> TYPE: PRT
<213> ORGANISM: Artificial Sequence
<220> FEATURE:
<223> OTHER INFORMATION: synthesized
<220> FEATURE:
```

```
<221> NAME/KEY: misc_feature
<223> OTHER INFORMATION: Humanized heavy chain variable region H10

<400> SEQUENCE: 17

Gln Val Lys Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ser Lys Asp Thr Ser Lys Ser Gln Val Phe Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser
        115                 120


<210> SEQ ID NO 18
<211> LENGTH: 107
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: FMC63 chimeric antibody light chain variable
      region

<400> SEQUENCE: 18

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr
            100                 105


<210> SEQ ID NO 19
<211> LENGTH: 120
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: FMC63 chimeric antibody heavy chain variable
      region

<400> SEQUENCE: 19

Glu Val Lys Leu Gln Glu Ser Gly Pro Gly Leu Val Ala Pro Ser Gln
```

```
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
        115                 120


<210> SEQ ID NO 20
<211> LENGTH: 108
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: BCMA scFv light chain variable region

<400> SEQUENCE: 20

Asp Ile Gln Met Thr Gln Ser Pro Ser Ser Val Ser Ala Ser Val Gly
1               5                   10                  15

Asp Arg Val Thr Ile Thr Cys Leu Ala Ser Glu Asp Ile Ser Asp Asp
            20                  25                  30

Leu Ala Trp Tyr Gln Gln Lys Pro Gly Lys Ala Pro Lys Val Leu Val
        35                  40                  45

Tyr Thr Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Thr Tyr Lys Phe Pro Pro
                85                  90                  95

Thr Phe Gly Gly Gly Thr Lys Val Glu Ile Lys Arg
            100                 105


<210> SEQ ID NO 21
<211> LENGTH: 121
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: BCMA scFv heavy chain variable region

<400> SEQUENCE: 21

Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Ile
        35                  40                  45
```

```
Gly Tyr Ile Asn Pro Asn Ser Gly Tyr Thr Asn Tyr Ala Gln Lys Phe
    50                  55                  60

Gln Gly Arg Ala Thr Met Thr Ala Asp Lys Ser Ile Asn Thr Ala Tyr
65                  70                  75                  80

Val Glu Leu Ser Arg Leu Arg Ser Asp Asp Thr Ala Val Tyr Phe Cys
                85                  90                  95

Thr Arg Tyr Met Trp Glu Arg Val Thr Gly Phe Phe Asp Phe Trp Gly
            100                 105                 110

Gln Gly Thr Met Val Thr Val Ser Ser
        115                 120


<210> SEQ ID NO 22
<211> LENGTH: 5
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: connecting peptide

<400> SEQUENCE: 22

Gly Gly Gly Gly Ser
1               5


<210> SEQ ID NO 23
<211> LENGTH: 21
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: CD8 signal peptide

<400> SEQUENCE: 23

Met Ala Leu Pro Val Thr Ala Leu Leu Leu Pro Leu Ala Leu Leu Leu
1               5                   10                  15

His Ala Ala Arg Pro
            20


<210> SEQ ID NO 24
<211> LENGTH: 45
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: CD8 hinge region

<400> SEQUENCE: 24

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45


<210> SEQ ID NO 25
<211> LENGTH: 24
<212> TYPE: PRT
<213> ORGANISM: Artificial Sequence
<220> FEATURE:
<223> OTHER INFORMATION: synthesized
```

```
<220> FEATURE:
<221> NAME/KEY: misc_feature
<223> OTHER INFORMATION: CD8 transmembrane region

<400> SEQUENCE: 25

Ile Tyr Ile Trp Ala Pro Leu Ala Gly Thr Cys Gly Val Leu Leu Leu
1               5                   10                  15

Ser Leu Val Ile Thr Leu Tyr Cys
            20


<210> SEQ ID NO 26
<211> LENGTH: 27
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: CD28 transmembrane region

<400> SEQUENCE: 26

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25


<210> SEQ ID NO 27
<211> LENGTH: 42
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: 41BB signal region

<400> SEQUENCE: 27

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40


<210> SEQ ID NO 28
<211> LENGTH: 41
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: CD28 signal region

<400> SEQUENCE: 28

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40


<210> SEQ ID NO 29
<211> LENGTH: 112
<212> TYPE: PRT
```

-continued

```
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: CD3z signal region

<400> SEQUENCE: 29

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110


<210> SEQ ID NO 30
<211> LENGTH: 20
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Self-cleaving 2A peptide

<400> SEQUENCE: 30

Gly Ser Gly Ala Thr Asn Phe Ser Leu Leu Lys Gln Ala Gly Asp Val
1               5                   10                  15

Glu Glu Asn Pro
            20
```